US008658568B2

(12) United States Patent
Eckelbarger et al.

(10) Patent No.: US 8,658,568 B2
(45) Date of Patent: Feb. 25, 2014

(54) 6-AMINO-2-SUBSTITUTED-5-VINYLSILYLPYRIMIDINE-4-CARBOXYLIC ACIDS AND ESTERS AND 4-AMINO-6-SUBSTITUTED-3-VINYLSILYLPYRIDINE-2-CARBOXYLIC ACIDS AND ESTERS AS HERBICIDES

(75) Inventors: Joseph D. Eckelbarger, Carmel, IN (US); Jeffrey B. Epp, Noblesville, IN (US); Paul R. Schmitzer, Indianapolis, IN (US)

(73) Assignee: Dow AgroSciences, LLC., Indianapolis, IN (US)

(*) Notice: Subject to any disclaimer, the term of this patent is extended or adjusted under 35 U.S.C. 154(b) by 198 days.

(21) Appl. No.: 13/356,729

(22) Filed: Jan. 24, 2012

(65) Prior Publication Data
US 2012/0190549 A1  Jul. 26, 2012

Related U.S. Application Data

(60) Provisional application No. 61/435,955, filed on Jan. 25, 2011.

(51) Int. Cl.
*A01N 55/10* (2006.01)
*C07F 7/08* (2006.01)
*C07F 7/02* (2006.01)

(52) U.S. Cl.
USPC ............... 504/193; 514/63; 544/229; 546/14

(58) Field of Classification Search
USPC ............... 504/193; 514/63; 544/229; 546/14
See application file for complete search history.

(56) References Cited

U.S. PATENT DOCUMENTS

2009/0088322 A1* 4/2009 Epp et al. .................. 504/243

* cited by examiner

*Primary Examiner* — James O Wilson
*Assistant Examiner* — Ebenezer O Sackey
(74) *Attorney, Agent, or Firm* — Robert Chang

(57) ABSTRACT

6-Amino-2-substituted-5-vinylsilylpyrimidine-4-carboxylates and 4-amino-6-substituted-3-vinylsilylpyridine-picolinates and their amine and acid derivatives are potent herbicides demonstrating a broad spectrum of weed control.

16 Claims, No Drawings

6-AMINO-2-SUBSTITUTED-5-VINYLSILYLPYRIMIDINE-4-CARBOXYLIC ACIDS AND ESTERS AND 4-AMINO-6-SUBSTITUTED-3-VINYLSILYLPYRIDINE-2-CARBOXYLIC ACIDS AND ESTERS AS HERBICIDES

CROSS REFERENCE TO RELATED APPLICATIONS

This application claims the benefit of U.S. Provisional Patent Application Ser. No. 61/435,955 filed Jan. 25, 2011.

FIELD OF THE INVENTION

This invention relates to 6-amino-2-substituted-5-vinylsilyl-pyrimidine-4-carboxylic acids and esters and 4-amino-6-substituted-3-vinylsilyl-pyridine-picolinic acids and esters and the use of such compounds as herbicides.

BACKGROUND OF THE INVENTION

A number of pyrimidine carboxylic acids and their pesticidal properties have been described in the art. WO 2005/063721 A1, WO 2007/092184 A2, WO 2007/08076 A1, WO 2009029735 A1, WO 2009/081112 A2, WO 2010/092339 A1, US Patent 2007/0197391 A1, U.S. Pat. Nos. 7,300,907 B2, 7,642,220 B2, and US 2009/0088322 A1 disclose genuses of 2-substituted-6-amino-4-pyrimidinecarboxylic acids and their derivatives with halogen, cyano, thiocyanato, nitro, alkyl, haloalkyl, alkenyl, haloalkenyl, alkoxy, thioalkyl and amino substituents in the 5-position and their use as herbicides.

Additionally, a number of picolinic acids and their pesticidal properties have been described in the art. WO 2001/051468 A1, WO 2003/011853 A1, WO 2006/062979 A1, US 2005/032651 A1, WO 2007/082098 A2, WO 2011/144891 A1, U.S. Pat. Nos. 6,297,197 B1; 6,784,137 B2; and 7,314,849 B2; and US Patent Application Publication 2004/0198608 A1, US 2009/0088322 A1 disclose genuses of 6-substituted-4-aminopicolinic acids and their derivatives with halogen, cyano, thiocyanato, nitro, alkyl, haloalkyl, alkenyl, haloalkenyl, alkoxy, haloalkoxy, thioalkyl and aryloxy substituents in the 3-position and their use as herbicides.

SUMMARY OF THE INVENTION

It has now been found that certain 2-substituted-6-amino-5-vinylsilyl-4-pyrimidinecarboxylic acids and 6-substituted-4-amino-3-vinylsilyl-picolinic acids and their derivatives are herbicides with a broad spectrum of weed control against woody plants, grasses and sedges as well as broadleaf weeds and with excellent selectivity to beneficial plant species. The compounds further possess excellent toxicological or environmental profiles.

Embodiments of the present invention include compounds of Formula I:

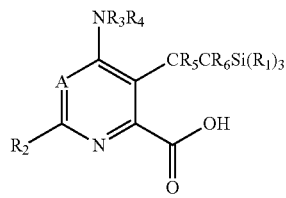

I wherein
A is selected from the group consisting of nitrogen and $CR_5$;
each $R_1$ is independently selected from the group consisting of $C_1$-$C_{10}$ alkyl, $C_3$-$C_6$ cycloalkyl, $C_1$-$C_{10}$ haloalkyl, $C_3$-$C_6$ halocycloalkyl, substituted or unsubstituted phenyl, $C_1$-$C_{10}$ alkoxy, and hydroxy ($R_1$ groups can but need not be equivalent);
$R_2$ is selected from the group consisting of $C_1$-$C_6$ alkyl, $C_3$-$C_6$ cycloalkyl, $C_1$-$C_6$ haloalkyl, $C_3$-$C_6$ halocycloalkyl, and

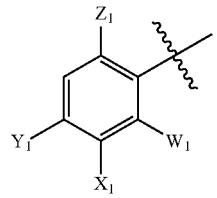

wherein
$W_1$ is selected from the group consisting of hydrogen and fluorine; $X_1$ is selected from the group consisting of hydrogen, halogen, $C_1$-$C_6$ alkyl, $C_2$-$C_6$ alkenyl, $C_2$-$C_6$ alkynyl, $C_1$-$C_6$ alkoxy, $C_2$-$C_4$ alkoxyalkyl, $C_2$-$C_6$ alkylcarbonyl, $C_1$-$C_6$ alkylthio, $C_1$-$C_6$ alkylsulfinyl, $C_1$-$C_6$ alkylsulfonyl, $C_2$-$C_4$ alkenyloxy, $C_2$-$C_4$ alkynyloxy, $C_2$-$C_4$ alkenylthio, $C_2$-$C_4$ alkynylthio, $C_1$-$C_6$ haloalkyl, $C_2$-$C_6$ haloalkenyl, $C_2$-$C_6$ haloalkynyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_4$ haloalkenyloxy, $C_2$-$C_4$ haloalkynyloxy, $C_2$-$C_4$ haloalkenylthio, $C_2$-$C_4$ haloalkynylthio, and —$N(R_7)_2$; $Y_1$ is selected from the group consiting of hydrogen, halogen, $C_1$-$C_6$ alkyl, $C_1$-$C_6$ haloalkyl, $C_1$-$C_6$ alkoxy, $C_1$-$C_6$ haloalkoxy, $Z_1$ is selected from the group consisting of hydrogen and fluorine; and wherein $X_1$ and $Y_1$ can represent —O($CH_2$)$_n$$CH_2$— or —O($CH_2$)$_n$O— wherein n=1 or 2;
$R_3$ and $R_4$ are selected independently from the group consisting of hydrogen, $C_1$-$C_6$ alkyl, $C_3$-$C_6$ alkenyl, $C_3$-$C_6$ alkynyl, hydroxy, $C_1$-$C_6$ alkoxy, amino, $C_1$-$C_6$ acyl, $C_1$-$C_6$ carboalkoxy, $C_1$-$C_6$ alkylcarbamyl, $C_1$-$C_6$ alkylsulfonyl, $C_1$-$C_6$ trialkylsilyl, and $C_1$-$C_6$ dialkyl phosphonyl;
$R_5$ is selected from the group consisting of hydrogen, fluorine, and chlorine, with the proviso that when A represents N, $X_1$ represents methoxy, and $W_1$ represents F, then $Y_1$ is not Cl;
$R_6$ is selected from the group consisting of hydrogen, fluorine, chlorine, $C_1$-$C_4$ alkyl, and $C_1$-$C_4$ haloalkyl;
$R_7$ is selected from the group consisting of hydrogen, $C_1$-$C_4$ alkyl and $C_1$-$C_4$ haloalkyl ($R_7$ groups can but need not be equivalent);
and agriculturally acceptable derivatives of the carboxylic acid group.

The invention includes herbicidal compositions comprising an herbicidally effective amount of a compound of Formula I and agriculturally acceptable derivatives of the carboxylic acid group in a mixture with an agriculturally acceptable adjuvant or carrier. The invention also includes a method of use of the compounds and compositions of the present invention to kill or control undesirable vegetation by application of an herbicidal amount of the compound to the vegetation or to the locus of the vegetation as well as to the soil prior to emergence of the vegetation. The invention further includes intermediates for the preparation of the compounds.

DETAILED DESCRIPTION OF THE INVENTION

The herbicidal compounds of the present invention are derivatives of 6-aminopyrimidine-4-carboxylic acids and 4-aminopicolinic acids of Formula I:

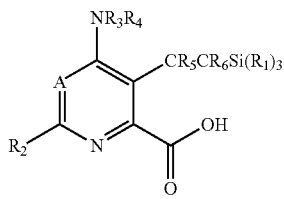

wherein

A is selected from the group consisting of nitrogen and $CR_5$;

each $R_1$ is independently selected from the group consisting of $C_1$-$C_{10}$ alkyl, $C_3$-$C_6$ cycloalkyl, $C_1$-$C_{10}$ haloalkyl, $C_3$-$C_6$ halocycloalkyl, substituted or unsubstituted phenyl, $C_1$-$C_{10}$ alkoxy, and hydroxy ($R_1$ groups can but need not be equivalent);

$R_2$ is selected from the group consisting of $C_1$-$C_6$ alkyl, $C_3$-$C_6$ cycloalkyl, $C_1$-$C_6$ haloalkyl, $C_3$-$C_6$ halocycloalkyl, and

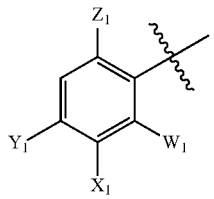

wherein $W_1$ is selected from the group consisting of hydrogen and fluorine; $X_1$ is selected from the group consisting of hydrogen, halogen, $C_1$-$C_6$ alkyl, $C_2$-$C_6$ alkenyl, $C_2$-$C_6$ alkynyl, $C_1$-$C_6$ alkoxy, $C_2$-$C_4$ alkoxyalkyl, $C_2$-$C_6$ alkylcarbonyl, $C_1$-$C_6$ alkylthio, $C_1$-$C_6$ alkylsulfinyl, $C_1$-$C_6$ alkylsulfonyl, $C_2$-$C_4$ alkenyloxy, $C_2$-$C_4$ alkynloxy, $C_2$-$C_4$ alkenylthio, $C_2$-$C_4$ alkynylthio, $C_1$-$C_6$ haloalkyl, $C_2$-$C_6$ haloalkenyl, $C_2$-$C_6$ haloalkynyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_4$ haloalkenyloxy, $C_2$-$C_4$ haloalkynyloxy, $C_2$-$C_4$ haloalkenylthio, $C_2$-$C_4$ haloalkynylthio, and —$N(R_7)_2$; $Y_1$ is selected from the group consiting of hydrogen, halogen, $C_1$-$C_6$ alkyl, $C_1$-$C_6$ haloalkyl, $C_1$-$C_6$ alkoxy, $C_1$-$C_6$ haloalkoxy; $Z_1$ is selected from the group consisting of hydrogen and fluorine; and wherein $X_1$ and $Y_1$ can represent —$O(CH_2)_nCH_2$— or —$O(CH_2)_nO$— wherein n=1 or 2

$R_3$ and $R_4$ are selected independently from the group consisting of hydrogen, $C_1$-$C_6$ alkyl, $C_3$-$C_6$ alkenyl, $C_3$-$C_6$ alkynyl, hydroxy, $C_1$-$C_6$ alkoxy, amino, $C_1$-$C_6$ acyl, $C_1$-$C_6$ carboalkoxy, $C_1$-$C_6$ alkylcarbamyl, $C_1$-$C_6$ alkylsulfonyl, $C_1$-$C_6$ trialkylsilyl, and $C_1$-$C_6$ dialkyl phosphonyl;

$R_5$ is selected from the group consisting of hydrogen, fluorine, and chlorine;

$R_6$ is selected from the group consisting of hydrogen, fluorine, chlorine, $C_1$-$C_4$ alkyl, and $C_1$-$C_4$ haloalkyl;

$R_7$ is selected from the group consisting of hydrogen, $C_1$-$C_4$ alkyl and $C_1$-$C_4$ haloalkyl ($R_7$ groups can but need not be equivalent);

and agriculturally acceptable derivatives of the carboxylic acid group.

The carboxylic acids of Formula I can kill or control undesirable vegetation and are typically preferred. Analogs of these compounds in which the acid group of the pyrimidine carboxylic acid or picolinic acid is derivatized to form a related substituent that can be transformed within plants or the environment to an acid group possess essentially the same herbicidal effect and are within the scope of the invention. Therefore, an "agriculturally acceptable derivative," when used to describe the carboxylic acid functionality at the 4-position of the pyrimidine ring or the 2-position of the pyridine ring, is defined as any salt, solvate, hydrate, ester, acylhydrazide, imidate, thioimidate, amidine, amide, orthoester, acylcyanide, acyl halide, thioester, thionoester, dithiolester, nitrile or any other acid derivative well known in the art which (a) does not substantially affect the herbicidal activity of the active ingredient, i.e., the 2-substituted-6-amino-5-vinylsilane-4-pyrimidinecarboxylic acid or the 6-substituted-4-amino-3-vinylsilane picolinic acid, and (b) is or can be hydrolyzed, oxidized or metabolized in plants or soil to the 6-aminopyrimidine-4-carboxylic acids or the 4-aminopicolinic acids of Formula I that, depending upon the pH, are in the dissociated or the undissociated form. Agriculturally acceptable derivatives of the carboxylic acid can include agriculturally acceptable salts, esters and amides. Likewise, an "agriculturally acceptable derivative," when used to describe the amine functionality at the 6- or 4-position, is defined as any salt, solvate, hydrate, silylamine, phosphorylamine, phosphinimine, phosphoramidate, sulfonamide, sulfilimine, sulfoximine, aminal, hemiaminal, amide, thioamide, carbamate, thiocarbamate, amidine, urea, imine, nitro, nitroso, azide, or any other nitrogen containing derivative well known in the art which (a) does not substantially affect the herbicidal activity of the active ingredient, i.e., the 2-substituted-6-amino-5-vinylsilyl-4-pyrimidinecarboxylic acid or the 6-substituted-4-amino-3-vinylsilyl picolinic acid, and (b) is or can be hydrolyzed in plants or soil to a free amine N-Oxides which are also capable of breaking into the parent pyrimidine or pyridine are also covered by the scope of this invention.

Suitable salts can include those derived from alkali or alkaline earth metals and those derived from ammonia and amines Preferred cations include sodium, potassium, magnesium, and aminium cations of the formula:

$$R_8R_9R_{10}R_{11}N^+$$

wherein $R_8$, $R_9$, $R_{10}$ and $R_{11}$ each, independently is hydrogen, $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R_8$, $R_9$, $R_{10}$ and $R_{11}$ are sterically compatible. Additionally, any two of $R_8$, $R_9$, $R_{10}$ and $R_{11}$ together may represent an aliphatic difunctional moiety containing 1 to 12 carbon atoms and up to two oxygen or sulfur atoms. Salts of the compounds of Formula I can be prepared by treatment of compounds of Formula I with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide Amine salts are often preferred forms of the compounds of Formula I because they are water-soluble and lend themselves to the preparation of desirable aqueous-based herbicidal compositions.

Suitable esters can include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols, such as methanol, iso-propanol, butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the 4-pyrimidine carboxylic acids or picolinic acids with the alcohol using any number of suitable activating agents such as those used for peptide couplings such as dicyclohexylcarbodiimide (DCC) or carbonyl diimidazole (CDI); by reacting 4-pyrimidine carboxylic acids or picolinic acids with alkylating agents such as alkylhalides or alkylsulfonates in the presence of a base such as triethylamine or lithium carbonate; by reacting the corresponding acid chloride of a 4-pyrimidinecarboxylic acid or picolinic acid of Formula I with an appropriate alcohol, by reacting the corresponding 4-pyrimidinecarboxylic acid or picolinic acid of Formula I with an appropriate alcohol in the presence of an acid catalyst or by transesterification.

Suitable amides include those derived from ammonia or from $C_1$-$C_{12}$ alkyl, $C_3$-$C_{12}$ alkenyl or $C_3$-$C_{12}$ alkynyl mono- or di-substituted amines, such as, but not limited to dimethylamine, diethanolamine, 2-methylthiopropyl-amine, bisallylamine, 2-butoxyethylamine, cyclododecylamine, benzylamine or cyclic or aromatic amines with or without additional heteroatoms such as but not limited to aziridine, azetidine, pyrrolidine, pyrrole, imidazole, tetrazole or morpholine, unsubstituted or substituted. Amides can be prepared by reacting the corresponding 4-pyrimidinecarboxylic acid or picolinic acid chloride, mixed anhydride, or carboxylic ester of Formula I with ammonia or an appropriate amine The terms "alkyl", "alkenyl", and "alkynyl", as well as derivative terms such as "alkoxy", "acyl", "alkylthio", and "alkylsulfonyl," as used herein, include within their scope straight chain and branched chain moieties, unsubstituted or substituted. The terms "alkenyl" and "alkynyl" are intended to include one or more unsaturated bonds. The term "aryl," as well as derivative terms such as "aryloxy," refers to a phenyl.

Unless specifically limited otherwise, the term "halogen" including derivative terms such as "halo" refers to fluorine, chlorine, bromine, and iodine. The terms "haloalkyl" and "haloalkoxy" refer to alkyl and alkoxy groups substituted with from 1 to the maximum possible number of halogen atoms.

The compounds of Formula I can be made using well-known chemical procedures. Intermediates not specifically mentioned in the above patent applications are either commercially available, can be made by routes disclosed in the chemical literature, or can be readily synthesized from commercial starting materials utilizing standard procedures.

As shown in Scheme 1, many 2-substituted-6-amino-5-vinylsilane-4-pyrimidinecarboxylic acid esters or 6-substituted-4-amino-3-vinylsilane picolinic acid esters of Formula I can be prepared by reaction of an appropriately substituted 5-halopyrimidine or 3-halopyridine of Formula II and an organometallic compound of type III in an inert solvent in the presence of a transition metal catalyst. In this case, Q can be chlorine, bromine or iodine; $R_1$ can be $C_1$-$C_{10}$ alkyl, $C_3$-$C_6$ cycloalkyl, $C_1$-$C_{10}$ haloalkyl, $C_3$-$C_6$ halocycloalkyl, substituted or unsubstituted phenyl or $C_1$-$C_{10}$ alkoxy ($R_1$ groups can but need not be equivalent); $R_2$ can be alkyl, cycloalkyl or aryl (including mono-, di-, tri-, and tetra-substituted or unsubstituted phenyl); $R_3$ and $R_4$ can be hydrogen, alkyl or acyl; $R_5$ can be hydrogen, fluorine or chlorine; $R_6$ can be hydrogen, fluorine, chlorine, $C_1$-$C_4$ alkyl or $C_1$-$C_4$ haloalkyl. M can be $Sn(R_{14})_3$, where $R_{14}$ can be $C_1$-$C_{10}$ alkyl, or; M can be $B(OR_{12})(OR_{13})$, where $R_{12}$ and $R_{13}$ are independent of one another and can be hydrogen, $C_1$-$C_6$ alkyl, or when taken together form an ethylene or propylene group; and "Catalyst" can be a transition metal catalyst, in particular a palladium catalyst such as palladium(II)acetate, bis(triphenylphosphine)palladium(II) dichloride or tetrakis triphenylphosphine palladium(0).

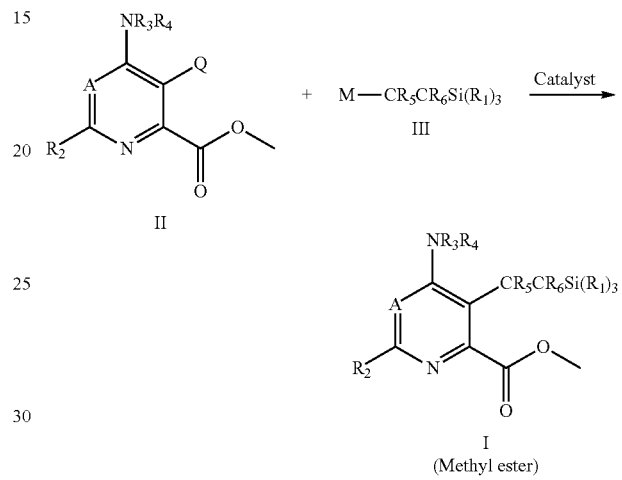

Scheme 1

Compounds of general formula IIIA can be prepared according to the method described in Example 1 of this document or the methods described in the following reference: Cunico, R. F.; Clayton, F. J. *J. Org. Chem.* 1976, 41, 1480-1482.

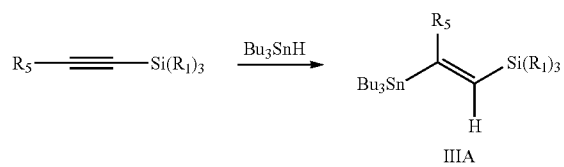

Compounds of general formula IIIB can be prepared according to the methods described in Examples 2 and 3 of this document.

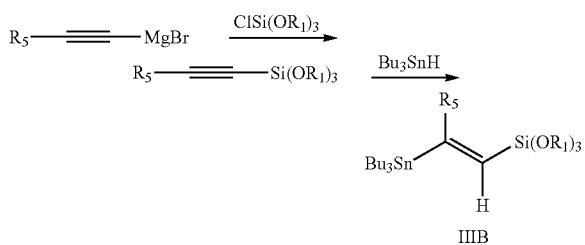

Compounds of general formula IIIC can be prepared according to the following refererence: Murakami, M.; Matsuda, T.; Itami, K.; Ashida, S.; Terayama, M. *Synthesis* 2004, 1522-1526.

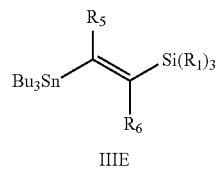

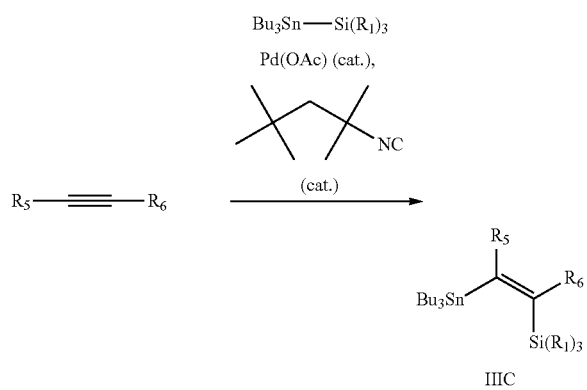

Compounds of general formula IIID can be prepared according to the following refererence: Suginome, M.; Nakamura, H.; Ito, Y. *Chem. Commun.* 1996, 2777-2778.

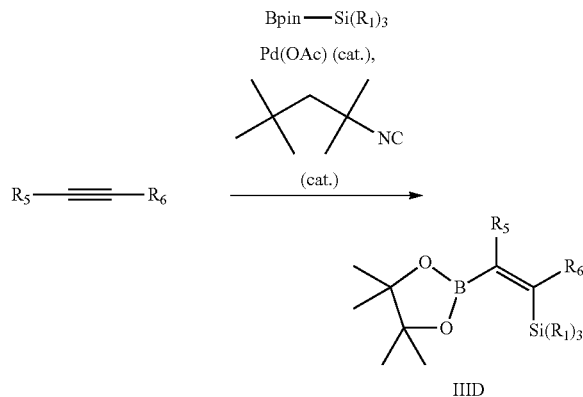

Compounds of general formula IIIE can be prepared according to the following refererence: Matthews, D. P.; Gross, R. S.; McCarthy, J. R. *Tetrahedron Lett.* 1994, 35, 1027-1030.

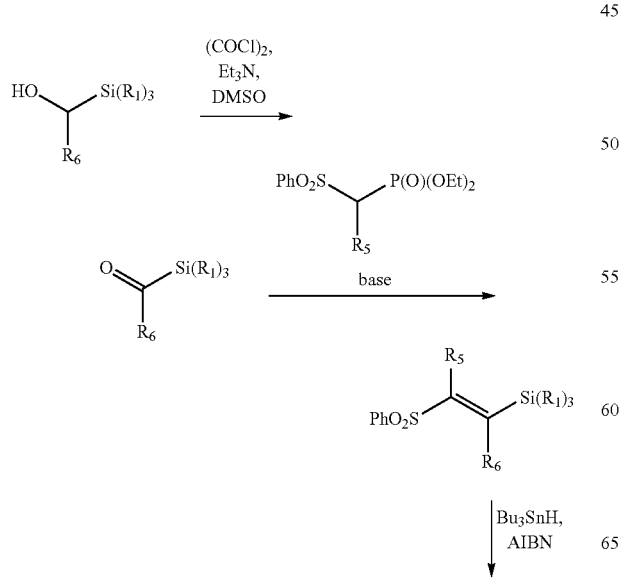

Compounds of general structure IIIF in which $R_5$ and/or $R_6$ are equal to chlorine or fluorine may be prepared preparation according to the following refererences: Beit-Yannai, M.; Rappoport, Z.; Shainyan, B. A.; Danilevich, Y. S. *J. Org. Chem.* 1997, 62, 8049-8057. Fontana, S.; Davis, C. R.; He, Y. B.; Burton, D. J. *Tetrahedron* 1996, 52, 37-44. Babudri, F.; Cardone, A.; De Cola, L.; Farinola, G. M.; Kottas, G. S.; Martinelli, C.; Naso, F. *Synthesis* 2008, 1580-1588.

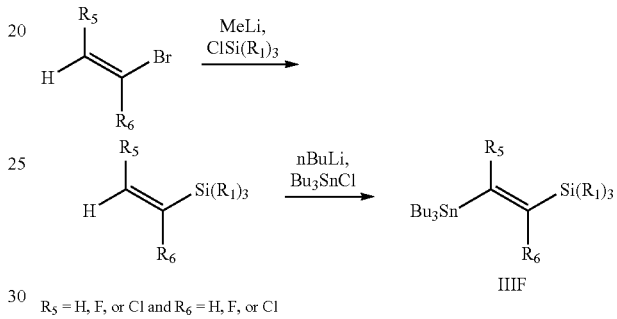

$R_5$ = H, F, or Cl and $R_6$ = H, F, or Cl

As shown in Scheme 2, many 2-substituted-6-amino-5-halo-4-pyrimidinecarboxylic acid esters or 6-substituted-4-amino-3-vinylsilane picolinic acid esters of Formula II can be made from compounds of Formula IV by reaction with a halogenating reagent such as bromine and a salt such as potassium acetate, or with a halogenating reagent such as N-bromosuccinimide in a solvent such as chloroform or acetonitrile. In this case, $R_2$ can be alkyl, cycloalkyl or aryl (including mono-, di-, tri-, and tetra-substituted or unsubstituted phenyl); $R_3$ and $R_4$ can be hydrogen or alkyl; and Q can be chlorine, bromine or iodine.

Scheme 2

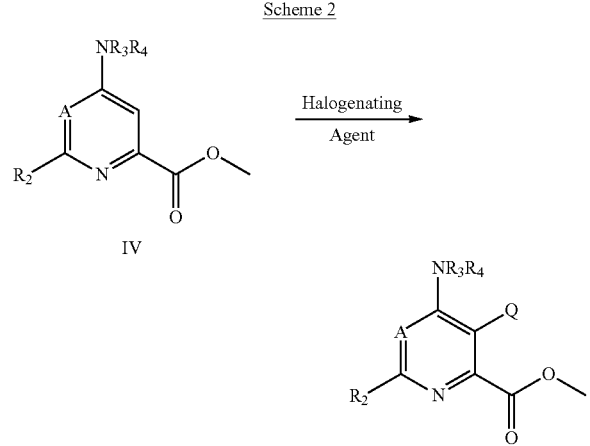

As shown in Scheme 3, many 2-substituted-6-amino-4-pyrimidinecarboxylic acid esters or 6-substituted-4-amino-3- vinylsilane picolinic acid esters of Formula IV can be prepared by reaction of appropriately substituted 2-chloropyrimidines or 6-chloropyridines of Formula V and an organometallic compound of type VI in an inert solvent in the presence of a transition metal catalyst. In this case, $R_2$ can be cyclopropyl or aryl (including mono-, di-, tri-, and tetra-substituted or unsubstituted phenyl); $R_3$ and $R_4$ can be hydrogen, alkyl or acyl; M can be $Sn(R_{14})_3$, where $R_{14}$ can be $C_1$-$C_{10}$ alkyl, or; M can be $B(OR_{12})(OR_{13})$, where $R_{12}$ and $R_{13}$ are independent of one another and can be hydrogen, $C_1$-$C_6$ alkyl, or when taken together form an ethylene or propylene group; and "Catalyst" can be a transition metal catalyst, in particular a palladium catalyst such as palladium(II)acetate, bis(triphenylphosphine)palladium(II) dichloride or tetrakis triphenylphosphine palladium(0).

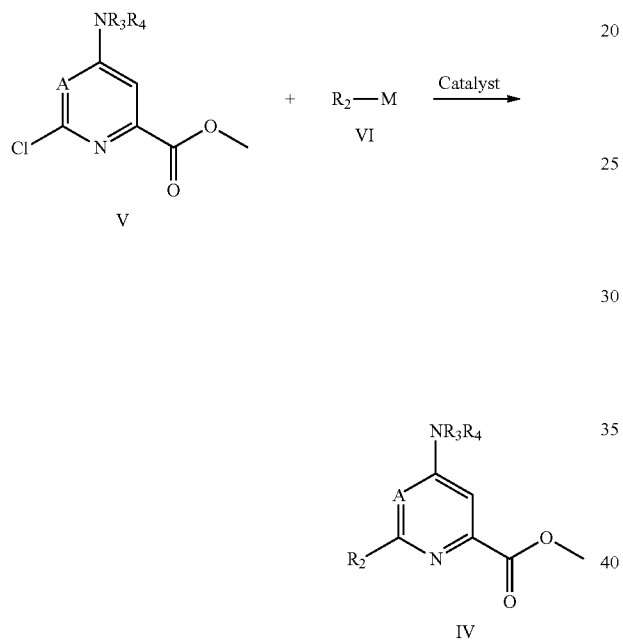

Scheme 3

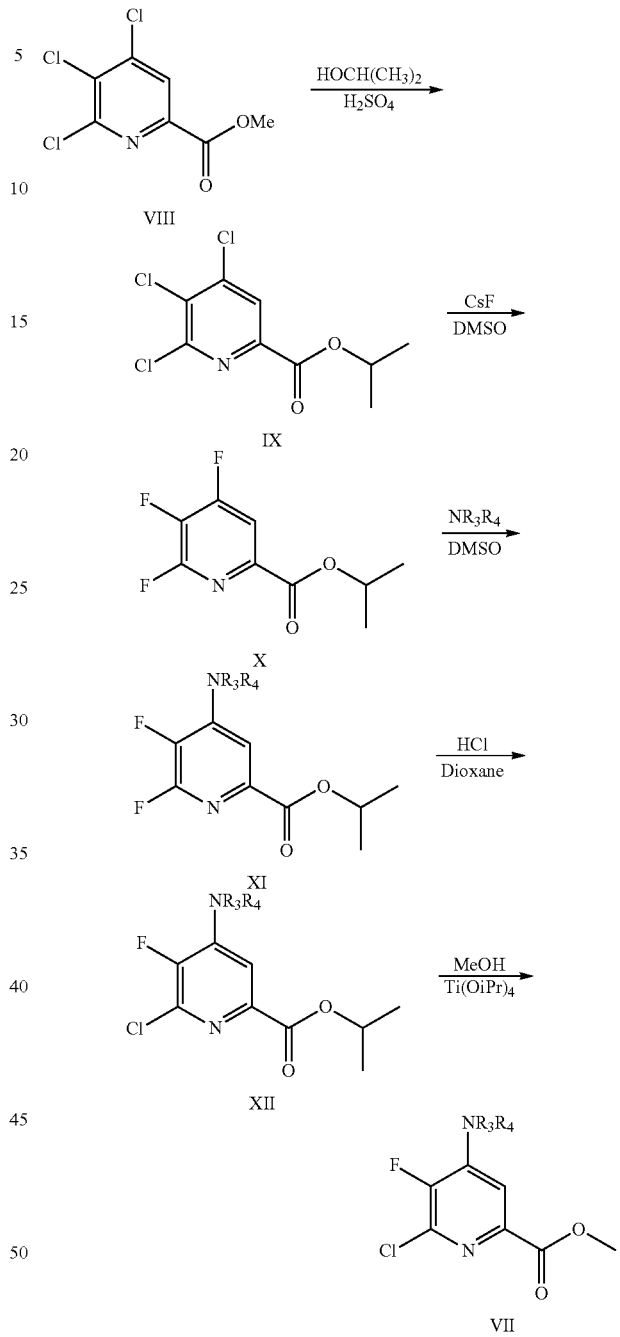

Scheme 4

As shown in Scheme 4, 5-fluoropicolinates of Formula VII can be synthesized from 4,5,6-trichloropicolinates of Formula VIII. Accordingly, methyl 4,5,6-trichloropicolinate of Formula VIII can be converted to the corresponding isopropyl ester of Formula IX by reaction with isopropyl alcohol and concentrated sulfuric acid at reflux temperature under Dean-Stark conditions. The isopropyl ester of Formula IX can be reacted with a fluoride ion source such as cesium fluoride in a polar, aprotic solvent such as dimethyl sulfoxide under Dean-Stark conditions to yield the isopropyl 4,5,6-trifluoropicolinate of Formula X. The isopropyl 4,5,6-trifluoropicolinate of Formula X can be aminated with a amine such as ammonia in a polar, aprotic solvent such as dimethyl sulfoxide to produce 4-amino-5,6-difluoropicolinates of Formula XI. The fluorine substituent in the 6-position of 4-amino-5,6-difluoropicolinates of Formula XI can be exchanged with a chlorine substituent by treatment with a chloride source, such as hydrogen chloride in solvent such as dioxane to produce 4-amino-5-fluoro-6-chloropicolinates of Formula XII. Finally, 4-amino-5-fluoro-6-chloropicolinates of Formula XII can be transesterified to the corresponding methyl esters of Formula VII by reaction with titanium(IV) isopropoxide in methyl alcohol at reflux temperature.

It is recognized that some reagents and reaction conditions disclosed herein or in the chemical literature for preparing compounds of Formula I may not be compatible with certain functionalities present in the intermediates. In these instances, the incorporation of protection/deprotection sequences or functional group interconversions into the synthesis will aid in obtaining the desired products. The use and choice of the protection groups will be apparent to one skilled in chemical synthesis.

One skilled in the art will recognize that, in some cases, after the introduction of a given reagent as disclosed herein or in the chemical literature, it may be necessary to perform additional routine synthetic steps not described in detail to complete the synthesis of compounds of Formula I. One skilled in the art will also recognize that it may necessary to perform a combination of the steps disclosed herein or in the chemical literature in an order other than that implied by the particular sequence presented to prepare the compounds of Formula I.

Finally, one skilled in the art will also recognize that compounds of Formula I and the intermediates described herein or in the chemical literature can be subjected to various electrophilic, nucleophilic, radical, organometallic, oxidation, and reduction reactions to add substituents or modify existing substituents.

4-N-Amide, carbamate, urea, sulfonamide, silylamine and phosphoramidate amino derivatives can be prepared by the reaction of the free amino compound with, for example, a suitable acid halide, chloroformate, carbamyl chloride, sulfonyl chloride, silyl chloride or chlorophosphate.

The compounds of Formula I, obtained by any of these processes, can be recovered by conventional means. Typically, the reaction mixture is acidified with an aqueous acid, such as hydrochloric acid, and extracted with an organic solvent, such as ethyl acetate or methylene chloride. The organic solvent and other volatiles can be removed by distillation or evaporation to obtain the desired compound of Formula I, which can be purified by standard procedures, such as by recrystallization or chromatography.

The compounds of Formula I have been found to be useful as pre-emergence and post-emergence herbicides. They can be employed at non-selective (higher) rates of application to control a broad spectrum of the vegetation in an area or at lower rates of application for the selective control of undesirable vegetation. Areas of application include pasture and rangelands, roadsides and rights of way, power lines and any industrial areas where control of undesirable vegetation is desirable. Another use is the control of unwanted vegetation in crops such as corn, rice and cereals. They can also be used to control undesirable vegetation in tree crops such as citrus, apple, rubber, oil palm, forestry and others. It is usually preferred to employ the compounds postemergence. It is further usually preferred to use the compounds to control a wide spectrum of woody plants, broadleaf and grass weeds, and sedges.

Use of the compounds to control undesirable vegetation in established crops is especially indicated. While each of the compounds encompassed by Formula I is within the scope of the invention, the degree of herbicidal activity, the crop selectivity, and the spectrum of weed control obtained varies depending upon the substituents present. An appropriate compound for any specific herbicidal utility can be identified by using the information presented herein and routine testing.

The term herbicide is used herein to mean an active ingredient that kills, controls or otherwise adversely modifies the growth of plants. An herbicidally effective or vegetation-controlling amount is an amount of active ingredient which causes an adversely modifying effect and includes deviations from natural development, killing, regulation, desiccation, retardation, and the like. The terms plants and vegetation include germinant seeds, emerging seedlings and established vegetation.

Herbicidal activity is exhibited by the compounds of the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the compounds of Formula I postemergence to relatively immature undesirable vegetation to achieve the maximum control of weeds.

Application rates of about 0.1 to about 1,000 g/Ha are generally employed in postemergence operations; for preemergence applications, rates of about 1 to about 2,000 g/Ha are generally employed. The higher rates designated generally give non-selective control of a broad variety of undesirable vegetation. The lower rates typically give selective control and can be employed in the locus of crops.

The herbicidal compounds of the present invention are often applied in conjunction with one or more other herbicides to control a wider variety of undesirable vegetation. When used in conjunction with other herbicides, the presently claimed compounds can be formulated with the other herbicide or herbicides, tank mixed with the other herbicide or herbicides or applied sequentially with the other herbicide or herbicides. Some of the herbicides that can be employed in conjunction with the compounds of the present invention include: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlomitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-P, glyphosate, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiocarbazil, tioclorim, topramezone, tralkoxydim, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac, tritosulfuron, vernolate, and xylachlor.

The compounds of the present invention can generally be employed in combination with known herbicide safeners, such as benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, isoxadifen-ethyl, mefenpyr-diethyl, MG 191, MON 4660, naphthalic anhydride (NA), oxabetrinil, R29148 and N-phenyl-sulfonylbenzoic acid amides, to enhance their selectivity.

The compounds of the present invention can additionally be employed to control undesirable vegetation in many crops that have been made tolerant to or resistant to them or to other herbicides by genetic manipulation or by mutation and selection. The herbicidal compounds of the present invention can, further, be used in conjunction with glyphosate, glufosinate, dicamba, imidazolinones or 2,4-D on glyphosate-tolerant, glufosinate-tolerant, dicamba-tolerant, imidazolinone-tolerant or 2,4-D-tolerant crops. It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix. Similarly the herbicidal compounds of the present invention can be used in conjunction with acetolactate synthase inhibitors on acetolactate synthase inhibitor tolerant crops.

While it is possible to utilize the 6-amino-2-substituted-5-vinylsilyl-pyrimidine-4-carboxylic acids and esters and 4-amino-6-substituted-3-vinylsilyl-pyridine-2-carboxylic acids and esters of Formula I directly as herbicides, it is preferable to use them in mixtures containing a herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate;

alcohol-alkylene oxide addition products, such as tridecyl alcohol-$C_{16}$ ethoxylate; soaps, such as sodium stearate; alkyl-naphthalene-sulfonate salts, such as sodium dibutylnaphthalenesulfonate; dialkyl esters of sulfo-succinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

The present compositions can be applied to weeds or their locus by the use of conventional ground or aerial dusters, sprayers, and granule applicators, by addition to irrigation water, and by other conventional means known to those skilled in the art.

The following Examples are presented to illustrate the various aspects of this invention and should not be construed as limitations to the claims.

EXAMPLES

Considerations: Fluorine spectra were acquired at 376 MHz on a Bruker DRX400 spectrometer. The spectra were referenced to trichlorofluoromethane ($CFCl_3$) as an external standard and were typically conducted with proton decoupling.

Example 1

Preparation of (E)-trimethyl(2-(tributylstannyl)vinyl)silane

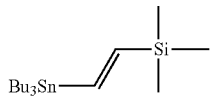

Tributyltin hydride (2.0 mL, 7.3 mmol, 1.0 equiv) and ethynyltrimethylsilane (2.1 mL, 15 mmol, 2.0 equiv) were combined, AIBN (60 mg, 0.36 mmol, 0.05 equiv) was added, and the resulting colorless neat solution was heated to 80° C. Upon heating, the reaction exothermed to ~110° C. The reaction mixture was cooled back to 80° C. and stirred for 20 h. The reaction mixture was cooled to 23° C. to afford the crude title compound as a pale yellow oil (2.8 g, 99% crude yield): $^1$H NMR (400 MHz, $CDCl_3$) δ 6.96 (d, J=22.5 Hz, 1H), 6.60 (d, J=22.5 Hz, 1H), 1.44-1.54 (m, 6H), 1.23-1.35 (m, 6H), 0.82-0.91 (m, 15H), 0.03 (s, 9H).

Example 2

Preparation of triethoxy(ethynyl)silane

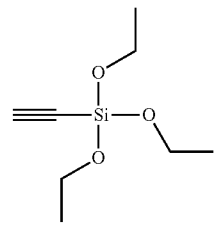

Chlorotriethoxysilane (2.0 mL, 10 mmol, 1.0 equiv) was added to a stirred solution of 0.5M ethynylmagnesium bromide (20 mL, 10 mmol, 1.0 equiv) in tetrahydrofuran (10 mL) at −78° C. The resulting heterogeneous light brown mixture was immediately warmed to 23° C. and stirred for 1 h. The resulting homogeneous light brown solution was heated to 50° C. and stirred for 4 h. The cooled reaction mixture was concentrated under vacuum. The resulting tan powder was slurried in hexane (50 mL), vacuum filtered, and rinsed with additional hexane (3×25 mL). The filtrates were dried over magnesium sulfate, gravity filtered, and concentrated under vacuum to provide the title compound as a pale yellow oil (1.5 g, 80% yield): IR (thin film) 3252 (w), 2976 (s), 2929 (m), 2913 (w), 2890 (m), 2046 (m) $cm^{-1}$; $^1$H NMR (400 MHz, $CDCl_3$) δ 3.90 (q, J=7 Hz, 6H), 2.35 (s, 1H), 1.23 (t, J=7 Hz, 9H).

Example 3

Preparation of (E)-triethoxy(2-(tributylstannyl)vinyl)silane

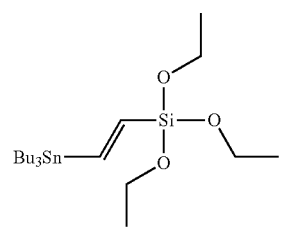

Tributyltin hydride (1.9 mL, 7.2 mmol, 1.0 equiv) and triethoxy(ethynyl)silane (1.5 g, 7.9 mmol, 1.1 equiv) were combined. AIBN (60 mg, 0.36 mmol, 0.05 equiv) was added and the resulting yellow solution was heated to 80° C. Upon reaching 80° C., the reaction exothermed to 104° C. The yellow solution was cooled back to 80° C. and stirred for 20 h. The reaction mixture was cooled to provide the title compound as a pale yellow oil (3.5 g, 99% crude yield): IR (thin film) 2957 (s), 2925 (s), 2873 (m), 2854 (m) $cm^{-1}$; $^1$H NMR (400 MHz, $CDCl_3$) δ 7.43 (d, J=24 Hz, 1H), 6.37 (d, J=24 Hz, 1H), 3.83 (q, J=7 Hz, 6H), 1.49 (m, 6H), 1.29 (m, 6H), 1.22 (t, J=7 Hz, 9 H), 0.82-0.92 (m, 15 H).

Example 4

Preparation of methyl 6-amino-2-(4-chloro-2,3-difluorophenyl)-pyrimidine-4-carboxylate

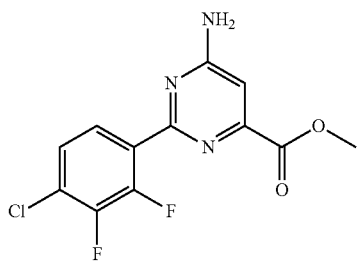 [SMILES: COC(=O)c1cc(N)nc(-c2ccc(Cl)c(F)c2F)n1]

2-(4-Chloro-2,3-difluorophenyl)-4,4,5,5-tetramethyl-1,3,2-dioxaborolane (1.4 g, 5.1 mmol, 1.2 equiv) and methyl 6-amino-2-chloropyrimidine-4-carboxylate (800 mg, 4.3 mmol, 1.0 equiv) were sequentially added to a 20 mL Biotage microwave vessel, followed by cesium fluoride (1.3 g, 8.5 mmol, 2.0 equiv), palladium(II) acetate (38 mg, 0.17 mmol, 0.04 equiv), and sodium 3,3',3''-phosphinetriyltribenzenesulfonate (190 mg, 0.34 mmol, 0.08 equiv). A 3:1 mixture of water:acetonitrile (8.5 mL) was added and the resulting brown mixture was placed in a Biotage microwave and heated at 150° C. for 5 m. The cooled reaction mixture was diluted with water (300 mL) and extracted with dichloromethane (5×100 mL). The combined organic layers were dried (magnesium sulfate), gravity-filtered, and concentrated under vacuum. The product was purified by flash chromatography (SiO$_2$, 40% ethyl acetate in hexane) to afford the title compound as an off-white powder (880 mg, 68% yield): mp 192-195° C.; $^1$H NMR (300 MHz, CDCl$_3$) δ 7.77 (m, 1H), 7.21-7.28 (m, 2H), 7.15 (s, 1H), 5.23 (br s, 2H), 4.00 (s, 3H); IR (neat film) 3493 (w), 3393 (m), 3342 (m), 3211 (s), 1730 (m), 1649 (m); ESIMS m/z 300 ([M+H]$^+$).

Example 5

Preparation of methyl 6-amino-5-bromo-2-(4-chloro-2,3-difluorophenyl)pyrimidine-4-carboxylate

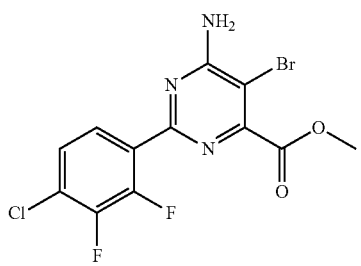 [SMILES: COC(=O)c1nc(-c2ccc(Cl)c(F)c2F)nc(N)c1Br]

Potassium acetate (750 mg, 7.6 mmol, 3.0 equiv) and bromine (150 μL, 2.8 mmol, 1.1 equiv) were sequentially added to a stirred suspension of methyl 6-amino-2-(4-chloro-2,3-difluorophenyl)pyrimidine-4-carboxylate (760 mg, 2.5 mmol, 1.0 equiv) in glacial acetic acid (10 mL) at 23° C. The resulting thick orange mixture was stirred at 23° C. for 2 h. The reaction mixture was quenched with saturated sodium thiosulfate solution (~50 mL) and adjusted to pH=7 using 50% sodium hydroxide solution. The resulting white mixture was diluted with water (150 mL) and extracted with dichloromethane (3×100 mL). The combined organic layers were dried (magnesium sulfate), gravity filtered, and concentrated under vacuum. The product was purified by flash chromatography (SiO$_2$, 33% ethyl acetate in hexane) to afford the title compound as a white powder (760 mg, 79% yield): mp 175-178° C.; $^1$H NMR (300 MHz, CDCl$_3$) δ 7.76 (ddd, 1H, J=9, 7, 2 Hz), 7.23 (ddd, 1H, J=9, 7, 2 Hz), 5.70 (br s, 2H), 4.01 (s, 3H); IR (neat film) 3473 (s), 3317 (s), 3179 (s), 2963 (w), 1740 (s), 1651 (s); ESIMS m/z 378 ([M+H]$^+$).

Example 6

Preparation of methyl 6-amino-2-(4-chloro-2-fluorophenyl)-5-iodopyrimidine-4-carboxylate

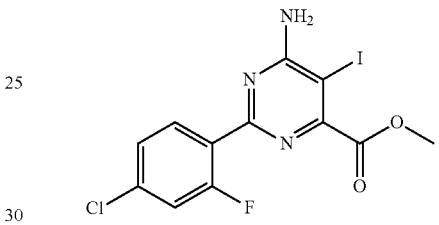

Methyl 6-amino-2-(4-chloro-2-fluorophenyl)pyrimidine-4-carboxylate (6.17 g, 21.91 mmol, see US 20090088322 for preparation) was diluted with methanol (100 ml). Periodic acid (2.10 g, 9.21 mmol) and iodine (5.26 g, 20.72 mmol) were added and the reaction was heated at reflux overnight. The cooled reaction mixture was diluted with dichloromethane and poured into a 1N solution of sodium sulfite. The aqueous phase was extracted with dichloromethane. The combined organic phases were washed with 1N sodium sulfite, washed with saturated sodium chloride, dried over magnesium sulfate, filtered, and concentrated onto celite. Purification by flash chromatography (SiO$_2$, 30% EtOAc:Hex) provided the title compound (1.46 g, 16% yield) as a white solid: $^1$H NMR (400 MHz, DMSO-d$_6$) d 3.89 (s, 3H), 7.34-7.46 (m, 1H), 7.53 (dd, J=10.7, 2.0 Hz, 1H), 7.89 (t, J=8.4 Hz, 1H); $^{19}$F NMR (376 MHz, DMSO-d6) d −110.23; ESIMS m/z 408 ([M+H]$^+$), 406 ([M−H]$^−$).

Another compound prepared by the method of Example 6 is:

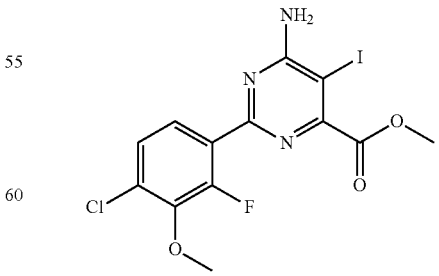

Methyl 6-amino-2-(4-chloro-2-fluoro-3-methoxyphenyl)-5-iodopyrimidine-4-carboxylate: $^1$H NMR (400 MHz, DMSO-d$_6$) d 3.89 (s, 3H), 3.91 (d, J=0.9 Hz, 3H), 7.41 (dd, J=8.7, 1.7 Hz, 1H), 7.61 (dd, J=8.7, 7.6 Hz, 1H); $^{19}$F NMR (376 MHz, DMSO-$d_6$) d −128.38; ESIMS m/z 438 ([M+H]$^+$), 436 ([M−H]$^−$).

Example 7

Preparation of (E)-methyl 6-amino-2-(4-chloro-2,3-difluorophenyl)-5-(2-(trimethylsilyl)vinyl)pyrimidine-4-carboxylate (Compound 1)

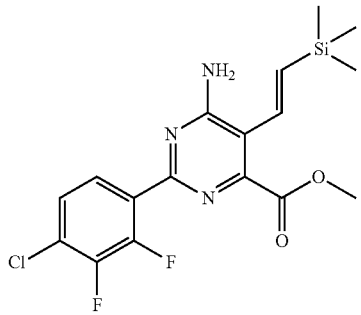

(E)-Trimethyl(2-(4,4,5,5-tetramethyl-1,3,2-dioxaborolan-2-yl)vinyl)silane (470 mg, 2.1 mmol, 1.2 equiv) and methyl 6-amino-5-bromo-2-(4-chloro-2,3-difluorophenyl)pyrimidine-4-carboxylate (650 mg, 1.7 mmol, 1.0 equiv) were sequentially added to a 5 mL Biotage microwave vessel, followed by cesium fluoride (260 mg, 1.7 mmol, 1.0 equiv), palladium(II) acetate (19 mg, 0.086 mmol, 0.05 equiv), and sodium 3,3',3''-phosphinetriyltribenzenesulfonate (98 mg, 0.17 mmol, 0.10 equiv). A 3:1 mixture of water:acetonitrile (3.5 mL) was added and the resulting brown mixture was placed in a Biotage microwave and heated to 150° C. for 15 m. The cooled reaction mixture was diluted with water (150 mL) and extracted with dichloromethane (3×50 mL). The combined organic layers were dried (magnesium sulfate), gravity filtered, and concentrated under vacuum. The product was purified by silica gel column chromatography (17% ethyl acetate in hexane) to afford the title compound as an off-white powder (290 mg, 43% yield): mp 139-141° C.; $^1$H NMR (300 MHz, CDCl$_3$) δ 7.76 (m, 1H), 7.22 (m, 1H), 6.94 (d, 1H, J=20 Hz), 6.37 (d, 1H, J=20 Hz), 5.38 (br s, 2H), 3.92 (s, 3H), 0.19 (s, 9H); IR (neat film) 3449 (m), 3350 (s), 3242 (m), 3103 (w), 2954 (m), 1728 (s), 1634 (s); ESIMS m/z 398 ([M+H]$^+$).

Another compound prepared by the method of Example 7 is:

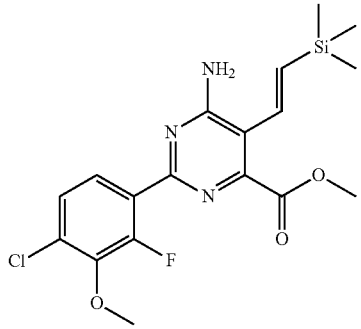

(E)-methyl 6-amino-2-(4-chloro-2-fluoro-3-methoxyphenyl)-5-(2-(trimethylsilyl)vinyl)-pyrimidine-4-carboxylate (Compound 2): mp 161-163° C.; $^1$H NMR (CDCl$_3$) δ 7.65 (dd, J=8, 9 Hz, 1H), 7.21 (dd, J=2, 9 Hz, 1H), 6.95 (d, J=19 Hz, 1H), 6.37 (d, J=19 Hz, 1H), 5.37 (br s, 2H), 4.00 (s, 3H), 3.92 (s, 3H), 0.19 (s, 9H); ESIMS m/z 410 ([M+H]$^+$).

Example 8

Preparation of (E)-methyl 6-amino-2-(4-chloro-2-fluorophenyl)-5-(2-(trimethylsilyl)vinyl)pyrimidine-4-carboxylate (Compound 3)

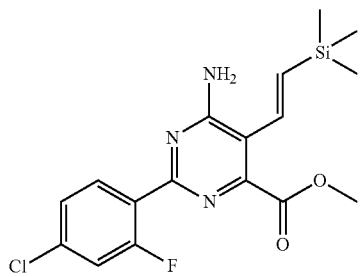 [SMILES: COC(=O)c1nc(-c2ccc(Cl)cc2F)nc(N)c1/C=C/[Si](C)(C)C]

Methyl 6-amino-2-(4-chloro-2-fluorophenyl)-5-iodopyrimidine-4-carboxylate (400 mg, 0.981 mmol) and tetrakis(triphenylphosphine)palladium(0) (113 mg, 0.098 mmol) were added to a 20 mL Biotage microwave reaction vessel. The vessel was sealed and purged with nitrogen gas. (E)-trimethyl(2-(tributylstannyl)vinyl)silane (497 mg, 1.276 mmol) in dioxane (4907 µl) was added and the reaction mixture was stirred overnight at 90° C. under nitrogen. The cooled reaction mixture was diluted with ethyl acetate and water. The organic phase was washed with saturated sodium chloride, dried over magnesium sulfate, filtered, and concentrated onto silica. Purification by flash chromatography (SiO$_2$, 0-20% EtOAc:Hex gradient) provided the title compound as a tan solid (0.283 g, 76% yield): $^1$H NMR (400 MHz, DMSO-$d_6$) d 0.16 (s, 9H), 3.78 (s, 3H), 6.14 (d, J=19.1 Hz, 1H), 6.80 (d, J=19.1 Hz, 1H), 7.21-7.68 (m, 4H), 7.92 (t, J=8.4 Hz, 1H); $^{19}$F NMR (376 MHz, DMSO-$d_6$) d −110.46; ESIMS m/z 380 ([M+H]$^+$), 378 ([M−H]$^−$).

Example 9

Preparation of (E)-ethyl 6-amino-2-cyclopropyl-5-(2-(trimethylsilyl)vinyl)pyrimidine-4-carboxylate (Compound 4)

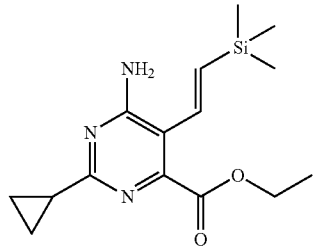 [SMILES: CCOC(=O)c1nc(C2CC2)nc(N)c1/C=C/[Si](C)(C)C]

Ethyl 6-amino-5-bromo-2-cyclopropylpyrimidine-4-carboxylate (0.5 g, 1.747 mmol, see WO 2005063721 for preparation) and tetrakis (triphenylphosphine) palladium(0) (0.214 g, 0.185 mmol) were added to a 20 mL Biotage microwave reaction vessel. The vessel was sealed and purged with nitrogen gas. (E)-trimethyl(2(tributylstannyl)vinyl)silane (0.96 g, 2.466 mmol) in dioxane (8.74 ml) was added and the reaction mixture was heated at 120° C. for 6 h. The cooled reaction mixture was diluted with ethyl acetate and water. The organic phase was washed with saturated sodium chloride, dried over magnesium sulfate, filtered, and concentrated onto silica. Purification by flash chromatography (SiO$_2$, 0-40% EtOAc: Hex gradient) provided the title compound as a tan solid (0.305 g, 57% yield): mp 99-101° C.; $^1$H NMR (400 MHz, DMSO-d6) δ 0.12 (s, 9H), 0.85-0.94 (m, 4H), 1.25 (t, J=7.1 Hz, 3H), 1.91 (tt, J=7.0, 5.6 Hz, 1H), 4.20 (q, J=7.1 Hz, 2H), 6.03 (d, J=19.1 Hz, 1H), 6.70 (d, J=19.2 Hz, 1H), 7.01 (s, 2H); ESIMS m/z 306 ([M+H]$^+$), 304 ([M−H]$^−$).

Example 10

Preparation of (E)-6-amino-2-(4-chloro-2,3-difluorophenyl)-5-(2-(trimethylsilyl)vinyl)pyrimidine-4-carboxylic acid (Compound 5)

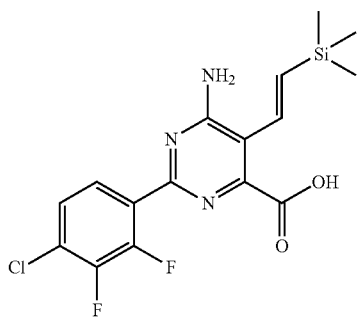 [SMILES: C[Si](C)(C)/C=C/c1c(N)nc(-c2ccc(Cl)c(F)c2F)nc1C(=O)O]

A 2M solution of aqueous sodium hydroxide (400 μL, 0.80 mmol, 2.0 equiv) was added to a stirred suspension of (E)-methyl 6-amino-2-(4-chloro-2,3-difluorophenyl)-5-(2-(trimethylsilyl)vinyl)pyrimidine-4-carboxylate (160 mg, 0.40 mmol, 1.0 equiv) in methanol (4.0 mL) at 23° C. The resulting heterogeneous yellow mixture was stirred at room temperature for 3 h. The reaction mixture was adjusted to approximately pH 4 via dropwise addition of concentrated hydrochloric acid and concentrated under vacuum. The residue was slurried in water and vacuum filtered to afford the title compound as an off-white powder (130 mg, 87%): mp 155-157° C.; $^1$H NMR (300 MHz, (CD$_3$)$_2$SO) δ 7.77 (m, 1H), 7.51 (m, 1H), 7.31 (br s, 2H); 6.77 (d, J=19 Hz, 1H), 6.30 (d, J=19 Hz, 1H), 0.12 (s, 9H); IR (neat) 3514 (s), 3475 (s), 3407 (s), 3336 (s), 3218 (m), 2963 (m), 1768 (m), 1640 (m), 1612 (m); ESIMS m/z 384 ([M+H]$^+$).

Other compounds prepared according to Example 10 above include:

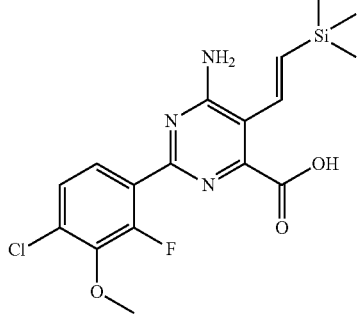

(E)-6-amino-2-(4-chloro-2-fluoro-3-methoxyphenyl)-5-(2-(trimethylsilyl)vinyl)pyrimidine-4-carboxylicacid (Compound 6): mp 108-110° C.; $^1$H NMR (DMSO-d$_6$) δ 7.62 (t, J=8 Hz, 1H), 7.39 (dd, J=2, 8 Hz), 7.29 (br s, 2H), 6.77 (d, 1H, J=19 Hz), 6.30 (d, 1H, J=19 Hz), 3.90 (s, 3H), 0.12 (s, 9H); ESIMS m/z 396 ([M+H]$^+$).

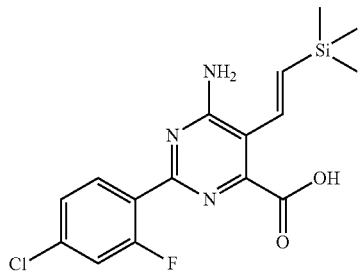 [SMILES: C[Si](C)(C)/C=C/c1c(N)nc(-c2ccc(Cl)cc2F)nc1C(=O)O]

(E)-6-amino-2-(4-chloro-2-fluorophenyl)-5-(2-(trimethylsilyl)vinyl)pyrimidine-4-carboxylic acid (Compound 7): $^1$H NMR (400 MHz, DMSO-d$_6$) d 0.16 (d, J=1.0 Hz, 9H), 6.33 (d, J=19.3 Hz, 1H), 6.80 (d, J=19.3 Hz, 1H), 7.04-7.49 (m, 3H), 7.54 (dd, J=10.7, 1.9 Hz, 1H), 7.94 (t, J=8.4 Hz, 1H). $^{19}$F NMR (376 MHz, DMSO-d$_6$) d −110.47; ESIMS m/z 367 ([M+H]$^+$).

Example 11

Preparation of (E)-6-amino-2-cyclopropyl-5-(2-(trimethylsilyl)vinyl)pyrimidine-4-carboxylic acid (Compound 8)

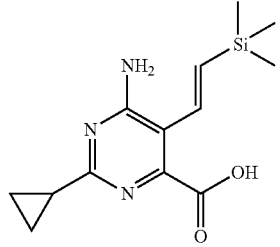 [SMILES: C[Si](C)(C)/C=C/c1c(N)nc(C2CC2)nc1C(=O)O]

(E)-ethyl 6-amino-2-cyclopropyl-5-(2-(trimethylsilyl)vinyl)pyrimidine-4-carboxylate (0.666 g, 2.180 mmol) was dissolved in THF (8.7 mL), MeOH (8.7 mL), and Water (4.4 mL). Lithium hydroxide hydrate (0.274 g, 6.54 mmol) was added as a solid. The reaction mixture was stirred for 15 min at room temperature. The solvent was removed under vacuum. The resulting solid was partitioned between 1 N HCl and ethyl acetate. The aqueous phase was extracted with ethyl acetate three times. The combined organics were washed with saturated sodium chloride, dried over magnesium sulfate, filtered, and concentrated. The solid was triturated with hexane (15 mL) and gently heated with heat gun. The solid from the resulting suspension was collected via filtration and dried under vaccum to provide the title compound as an off-white solid (0.104 g, 17% yield): mp 146-149° C.; $^1$H NMR (400 MHz, DMSO-d6) δ 0.12 (s, 9H), 0.91-1.03 (m, 4H), 2.02 (tt, J=7.8, 5.1 Hz, 1H), 6.22 (d, J=19.3 Hz, 1H), 6.74 (d, J=19.3 Hz, 1H), 7.34 (s, 2H); ESIMS m/z 278 ([M+H]$^+$), 276 ([M−H]$^−$)

Example 12

Preparation of (E)-methyl 6-amino-2-(4-chloro-2-fluoro-3-methoxyphenyl)-5-(2-(triethoxysilyl)vinyl)pyrimidine-4-carboxylate (Compound 9)

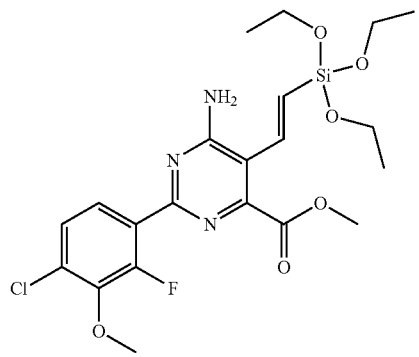 [SMILES: CCO[Si](/C=C/c1c(N)nc(-c2ccc(Cl)c(OC)c2F)nc1C(=O)OC)(OCC)OCC]

Tetrakis triphenylphosphine palladium(0) (160 mg, 0.14 mmol, 0.10 equiv) and (E)-triethoxy(2-(tributylstannyl)vinyl)silane (990 mg, 2.1 mmol, 1.5 equiv) were sequentially added to a stirred solution of methyl 6-amino-2-(4-chloro-2-fluoro-3-methoxyphenyl)-5-iodopyrimidine-4-carboxylate (600 mg, 1.4 mmol, 1.0 equiv) in N,N-dimethylformamide (5.5 mL) at room temperature. The heterogeneous yellow mixture was heated at 90° C. and stirred for 5 d. The cooled reaction mixture was diluted with water (300 mL) and extracted with diethyl ether (3×100 mL). The combined organic layers were dried (magnesium sulfate), gravity filtered, and concentrated under vacuum. The product was purified by acid free reverse phase column chromatography (5% acetonitrile to 100% acetonitrile gradient) to provide the title compound as a yellow glass (38 mg, 6% yield): IR (thin film) 3315 (w), 3069 (w), 2974 (w), 1657 (s) cm$^{-1}$; $^1$H NMR (400 MHz, CDCl$_3$) δ 7.66 (dd, J=9, 8 Hz, 1H), 7.29 (d, J=18.5 Hz, 1H), 7.21 (dd, J=9, 2 Hz, 1H), 6.06 (d, J=18.5 Hz, 1H), 5.39 (br s, 2H), 3.98 (d, J=1 Hz, 3H), 3.92 (s, 3H), 3.89 (q, J=7 Hz, 6H), 1.26 (t, J=7 Hz, 9H); ESIMS m/z 500 [(M+H)$^+$].

Example 13

(E)-6-amino-2-(4-chloro-2-fluoro-3-methoxyphenyl)-5-(2-(trihydroxysilyl)vinyl)pyrimidine-4-carboxylic acid (Compound 10)

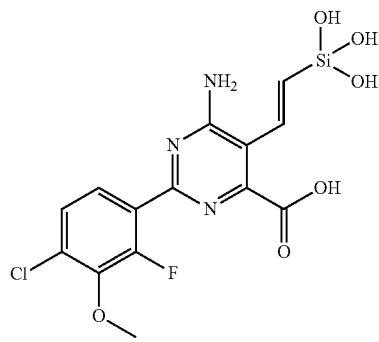 [SMILES: COc1c(Cl)ccc(-c2nc(N)c(/C=C/[Si](O)(O)O)c(C(=O)O)n2)c1F]

A 2M aqueous solution of sodium hydroxide (150 µL, 0.31 mmol, 1.05 equiv) was added to a stirred solution of (E)-methyl 6-amino-2-(4-chloro-2-fluoro-3-methoxyphenyl)-5-(2-(triethoxysilyl)vinyl)pyrimidine-4-carboxylate (145 mg, 0.29 mmol, 1.0 equiv) in 3:1 methanol:tetrahydrofuran (4.0 mL) at room temperature. The homogeneous yellow solution was stirred at room temperature for 20 h. The reaction mixture was adjusted to pH 4 using concentrated hydrochloric acid and concentrated under vacuum. The residue was slurried in water and vacuum filtered to provide the title compound as a tan powder (95 mg, 81% yield): mp 220-250° C. (decomposition); IR (thin film) 3323 (m), 3195 (m), 2944 (w), 1603 (s), 1534 (s) cm$^{-1}$; $^1$H NMR (400 MHz, DMSO-d$_6$) δ 7.56-7.76 (m, 1H), 6.59-7.52 (m, 4H), 3.93 (br s, 3H); ESIMS m/z 402 [(M+H)$^+$].

Example 14

Preparation of propan-2-yl 4,5,6-trichloropicolinate

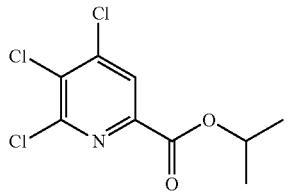

Methyl 4,5,6-trichloropicolinate (prepared as in Balko, T. W. et al. U.S. Pat. No. 6,784,137 B2, Aug. 31, 2004; 14.19 g, 59.0 mmol) was slurried in 2-propanol (150 mL) in a 250 mL round bottom flask equipped with a Dean-Stark trap and a reflux condenser. Sulfuric acid (98% H$_2$SO$_4$; 8.07 g, 82 mmol) was added, and the reaction mixture was heated to reflux. After 20 h at reflux, the majority of the 2-propanol (100 mL) was distilled overhead. The remaining reaction mixture solidified upon cooling to room temperature. The resulting solid was stirred with EtOAc (500 mL) and satd aq NaHCO$_3$ (500 mL). The organic layer was separated, washed with satd aq NaCl, and then filtered through Celite. The organic extract was concentrated to 150 mL by rotary evaporation. Hexane (100 mL) was added, and the solution was stored at −20° C. overnight. Crystals were collected, washed with hexane and dried in air (7.58 g, mp 104.6-105.7° C.). A second crop was obtained by concentration of the filtrate to give a total of 10.36 g (65%): $^1$H NMR (400 MHz, DMSO-d$_6$) δ 8.23 (s, 1H, pyridine H), 5.16 (septet, J=6.3 Hz, 1H, CHMe$_2$), 1.34 (d, J=6.3 Hz, 6H, CHMe$_2$); $^{13}$C{$^1$H} NMR (101 MHz, CDCl$_3$) δ 161.9 (CO$_2$R), 150.6, 145.9, 145.0, 133.1, 125.4 (C3), 70.7 (CHMe$_2$), 21.7 (Me). Anal. Calcd for C$_9$H$_8$Cl$_3$NO$_2$: C, 40.26; H, 3.00; N, 5.22. Found: C, 40.25; H, 3.02; N, 5.22.

Example 15

Preparation of propan-2-yl 4,5,6-trifluoropicolinate

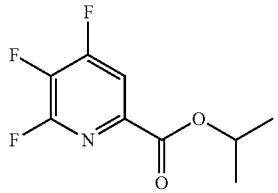

A 250 mL three-neck flask was equipped with a mechanical stirrer, a Dean-Stark trap with nitrogen inlet, and a thermocouple. The flask was purged with nitrogen and CsF (23.38 g, 154 mmol) was added. Anhydrous DMSO (124 mL) was added and the suspension was evacuated/backfilled (5×) with nitrogen. The suspension was heated at 80° C. for 30 min DMSO (20 mL) was distilled off under vacuum at 75° C. to remove any residual water. Propan-2-yl 4,5,6-trichloropicolinate (13.45 g, 50.1 mmol) was added against a nitrogen purge. The reaction mixture was evacuated/backfilled (3×) and heated at 100° C. for 1 h with vigorous stirring.

A second 250 mL three-neck flask was equipped with a mechanical stirrer, a Dean-Stark trap with nitrogen inlet, and a thermocouple. The flask was purged with nitrogen and CsF (24.41 g, 0.160 mmol) was added. Anhydrous DMSO (30 mL) was added, and the suspension was evacuated/backfilled (5×) with nitrogen. The suspension was heated to 80° C. for 30 min DMSO (22 mL) was distilled off under vacuum at 75° C. to remove residual water. The cooled reaction mixture in the first flask was cannula filtered into the second flask under nitrogen. The reaction mixture was evacuated/backfilled (5×) and then heated at 100° C. for 1 h and then for an additional 90 min at 110° C. Analysis of an aliquot by gas chromatography (GC) showed 96% propan-2-yl 4,5,6-trifluoropicolinate with only 1.4% propan-2-yl 5-chloro-4,6-difluoropicolinate present. The crude product solution was used directly in the amination step without further purification. Alternatively, the product can be isolated by aqueous workup, extraction with EtOAc, and drying to give a light tan oil: $^1$H NMR (400 MHz, CDCl$_3$) δ 7.94 (dd, $J_{F-H}$=4.5, 8.7 Hz, 1H, H3), 5.30 (septet, $J_{H-H}$=6.3 Hz, 1H, CHMe$_2$), 1.44 (d, $J_{H-H}$=6.3 Hz, 6H, CHMe$_2$); $^{13}$C{$^1$H} NMR (101 MHz, CDCl$_3$) δ 161.2 (s, CO$_2$iPr), 157.3 (ddd, $J_{F-C}$=266, 8, 6 Hz, C4/C6), 152.2 (ddd, $J_{F-C}$=241, 12, 5 Hz, C4/C6), 141.1 (dt, $J_{F-C}$=14, 7 Hz, C2), 137.0 (ddd, $J_{F-C}$=270, 31, 13 Hz, C5), 113.8 (dd, $J_{F-C}$=17, 4 Hz, C3), 70.4 (s, CHMe$_2$), 21.33 (s, Me); $^{19}$F NMR (376 MHz, CDCl$_3$) δ -74.29 (dd, $J_{F-F}$=24, 22 Hz, F6), -112.67 (ddd, $J_{F-F}$=22, 19, $J_{F-H}$=8.3 Hz, F4), -151.58 (ddd, $J_{F-F}$=24, 19, $J_{F-H}$=4.7 Hz, F5).

Example 16

Preparation of propan-2-yl 4-amino-5,6-trifluoropicolinate

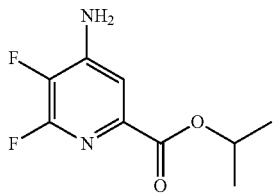

The reaction mixture from Example 21 was filtered to remove Cs salts, and the salts were washed with DMSO (50 mL). The DMSO washing solution was added to the DMSO solution (150 mL) which had been saturated with ammonia (NH$_3$) for 15 min. The flask was kept in a cold bath which kept the temperature near 16° C. NH$_3$ was bubbled through the reaction mixture for 30 min, during which time a white precipitate formed. After 90 min, analysis of an aliquot by GC showed a single major peak for the 4-amino product. The reaction mixture was quenched by addition of satd aq NH$_4$Cl (100 mL), followed by H$_2$O (400 mL). The aqueous solution was extracted into Et$_2$O (3×150 mL) and then EtOAc (3×150 mL). The combined organic extracts were washed with H$_2$O (5×150 mL) and then satd aq NaCl. The extracts were dried (MgSO$_4$) and evaporated to a tan solid, which was washed with 1:1 hexane-Et$_2$O to give a light tan powder (5.57 g, 51.4% overall): mp 168-170° C.; $^1$H NMR (400 MHz, CDCl$_3$) δ 7.42 (d, $J_{F-H}$=5.5 Hz, 1H, pyridine H), 5.22 (septet, J=6.2 Hz, 1H, CHMe$_2$), 4.75 (s, 2H, NH$_2$), 1.35 (d, J=6.2 Hz, 6H, CHMe$_2$); $^{13}$C{$^1$H} NMR (101 MHz, DMSO-d$_6$) δ 162.8 (CO$_2$R), 151.2 (dd, $J_{F-C}$=228, 12 Hz, C6), 146.5 (dd, $J_{F-C}$=9, 6 Hz, C2/C4), 139.3 (dd, $J_{F-C}$=16, 5 Hz, C2/C4), 133.8 (dd, $J_{F-C}$=252, 31 Hz, C5), 112.3 (C3), 68.8 (CHMe$_2$), 21.5 (Me); $^{19}$F NMR (376 MHz, DMSO-d$_6$) δ -91.9 (d, $J_{F-F}$=26.6 Hz, F6), -163.9 (dd, $J_{F-F}$=26.6, $J_{H-F}$=5.6 Hz, F5). Anal. Calcd for C$_9$H$_{10}$F$_2$N$_2$O$_2$: C, 50.00; H, 4.66; N, 12.96. Found: C, 49.96; H, 4.65; N, 12.91.

Example 17

Preparation of propan-2-yl 4-amino-6-chloro-5-fluoropicolinate

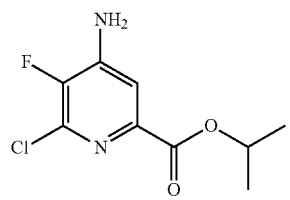

Propan-2-yl 4-amino-5,6-difluoropicolinate (4.25 g, 19.7 mmol) was dissolved in HCl (4 M in dioxane; 65 mL) in a 100 mL Hastalloy stirred Parr reactor. The reactor was heated at 100° C. for 2 h. Upon standing at room temperature overnight, a yellow crystalline solid formed. This solid was not soluble in EtOAc but did dissolve upon shaking with satd aq NaHCO$_3$ (500 mL) and EtOAc (300 mL). The aqueous layer was extracted with EtOAc (2×250 mL). The combined organic extracts were washed with H$_2$O (5×50 mL) and then with satd aq NaCl. The extracts were dried (MgSO$_4$) and concentrated under vacuum to provide an off-white solid. The crude product was purified by column chromatography (120 g silica column; 0-100% hexane-EtOAc gradient) to give a white solid (2.11 g, 46%): mp 190.7-192.4° C.; $^1$H NMR (400 MHz, DMSO-d$_6$) δ 7.543 (d, $J_{F-H}$=5.7 Hz, 1H), 6.91 (br s, 2H, NH$_2$), 5.09 (septet, J=6 Hz, 1H, CHMe$_2$), 1.29 (d, J=6 Hz, 6H, CHMe$_2$); $^{13}$C{$^1$H} NMR (101 MHz, DMSO-d$_6$) δ 162.8 (CO$_2$R), 144.8 (d, $J_{F-C}$=12 Hz, C2/C4), 143.4 (d, $J_{F-C}$=254 Hz, C5), 142.7 (d, $J_{F-C}$=4.8 Hz, C2/C4), 136.5 (d, $J_{F-C}$=17 Hz, C6), 112.8 (d, $J_{F-C}$=5 Hz, C3), 68.9 (CHMe$_2$), 21.6 (Me); $^{19}$F NMR (376 MHz, DMSO-d$_6$) δ -141.0 (d, $J_{F-H}$=6 Hz). Anal. Calcd for C$_9$H$_{10}$ClFN$_2$O$_2$: C, 46.47; H, 4.33; N, 13.75. Found: C, 46.50; H, 4.33; N, 11.96.

Example 18

Preparation of methyl 4-amino-6-chloro-5-fluoropicolinate

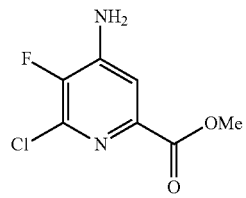 [SMILES: COC(=O)c1cc(N)c(F)c(Cl)n1]

Isopropyl 4-amino-6-chloro-5-fluoropicolinate (1.35 g, 5.80 mmol) was dissolved in anhydrous CH$_3$OH (50 mL), treated with titanium(IV) isopropoxide (300 mg, 2.2 mmol), and heated at reflux for 4 h. After cooling, the volatiles were removed under vacuum, and the residue was taken up in EtOAc (30 mL). This solution was stirred with H$_2$O (1 mL) for 20 min and then filtered through diatomaceous earth. The filtrate was washed with satd aq NaCl (10 mL), dried (Na$_2$SO$_4$), and evaporated to give the title compound (1.2 g, 97%): mp 180-183° C.; $^1$H NMR (400 MHz, DMSO-d$_6$) δ 7.45 (d, J=6.0 Hz, 1H), 6.93 (s, 2H), 3.83 (s, 3H); $^{19}$F NMR (376 MHz, DMSO-d$_6$) δ −131.36, −131.42, −135.47, −135.53; EIMS m/z 204.

Example 19

Preparation of methyl 4-amino-6-(4-chloro-3-fluorophenyl)-5-fluoropicolinate

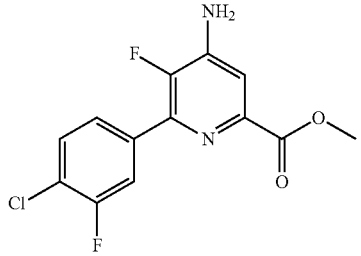 [SMILES: COC(=O)c1cc(N)c(F)c(-c2ccc(Cl)c(F)c2)n1]

Methyl 4-amino-6-chloro-5-fluoropicolinate (3.0 g, 14.66 mmol), (4-chloro-3-fluorophenyl)boronic acid (3.07 g, 17.60 mmol), bis(triphenylphosphine)palladium(II) dichloride (1.029 g, 1.466 mmol), and cesium fluoride (4.45 g, 29.3 mmol) were comined in a flask that was sealed and purged with nitrogen. Dioxane (50 ml) and Water (10.00 ml) were added and the reaction mixture was heated at 85° C. for 18 hrs. The reaction mixture was diluted with ethyl acetate and water. The organic phase was washed with saturated sodium chlride, dried over magnesium sulfate, filtered, and concentrated onto silica. The product was purified by flash chromatography (SiO$_2$, 0-40% EtOAc:Hex gradient) to provide the title compound (3.11 g, 10.41 mmol, 71.0% yield) as a white solid: $^1$H NMR (400 MHz, DMSO-d$_6$) d 3.85 (s, 3H), 6.72 (s, 2H), 7.49 (d, J=6.3 Hz, 1H), 7.68-7.80 (m, 2H), 7.84 (dd, J=10.8, 1.3 Hz, 1H); $^{19}$F NMR (376 MHz, DMSO-d$_6$) d −144.47, −116.07; ESIMS m/z 299 ([M+H]$^+$).

Another compound prepared by the method of Example 19 is:

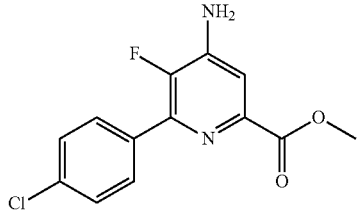 [SMILES: COC(=O)c1cc(N)c(F)c(-c2ccc(Cl)cc2)n1]

Methyl 4-amino-6-(4-chlorophenyl)-5-fluoropicolinate: mp 174-175° C.; $^1$H NMR (400 MHz, CDCl$_3$) δ 7.95-7.82 (m, 2H), 7.52 (d, J=6.2 Hz, 1H), 7.48-7.38 (m, 2H), 4.51 (s, 2H), 3.96 (s, 3H); $^{19}$F NMR (376 MHz, CDCl$_3$) δ −145.13 (s); ESIMS m/z 281 ([M+H]$^+$).

Example 20

Preparation of methyl 4-amino-5-fluoro-6-vinylpicolinate

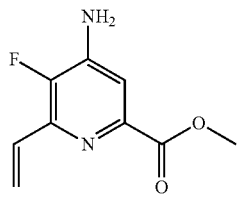

Methyl 4-amino-6-chloro-5-fluoropicolinate (1.9 g, 9.29 mmol) and bis(triphenylphosphine)palladium(II) dichloride (0.326 g, 0.464 mmol) were combined in dichloroethane (30 ml) and tributyl(vinyl)stannane (3.26 ml, 11.14 mmol) was added. The reaction mixture was heated in a microwave reactor at 140° C. for 2 hrs. The cooled reaction mixture was purified by flash chromatography (SiO2, 0-40% THF:Hex gradient) to provide the title compound as a white solid (0.9 g, 4.59 mmol, 49.4% yield): $^1$H NMR (400 MHz, DMSO-d6) δ 3.83 (s, 3H), 5.57 (dd, J=10.9, 2.2 Hz, 1H), 6.28 (dd, J=17.3, 2.2 Hz, 1H), 6.54 (s, 2H), 6.84-6.97 (m, 1H), 7.37 (d, J=6.7 Hz, 1H); $^{19}$F NMR (376 MHz, DMSO-d6) δ −148.25; ESIMS m/z 197 ([M+H]$^+$), 195 ([M−H]$^−$).

Example 21

Preparation of methyl 4-amino-6-ethyl-5-fluoropicolinate

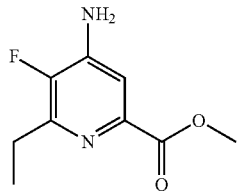

Pd/C (0.976 g, 0.459 mmol) was added to a 500 mL Parr bottle and methyl 4-amino-5-fluoro-6-vinylpicolinate (0.9 g, 4.59 mmol) dissolved in ethanol (50 ml) was added. The Parr bottle was placed on a Parr shaker, purged with nitrogen gas three times, and pressurized to 43 psi with hydrogen gas. The reaction mixture was shaken on the Parr Shaker for 45 min The catalyst was removed via filtration through celite. The celite was washed with ethyl acetate. The filtrates were combined and concentrated under vacuum to provide the title compoud as a white solid (820 mg, 4.14 mmol, 90% yield); $^1$H NMR (400 MHz, DMSO-d6) δ 1.17 (t, J=7.6 Hz, 3H), 2.68 (qd, J=7.6, 2.7 Hz, 2H), 3.80 (s, 3H), 6.39 (s, 2H), 7.34

(d, J=6.7 Hz, 1H; ¹⁹F NMR (376 MHz, DMSO-d6) δ −147.65; ESIMS m/z 199 ([M+H]⁺), 197 ([M−H]⁻).

Example 22

Preparation of methyl 4-amino-6-(4-chloro-3-fluorophenyl)-5-fluoro-3-iodopicolinate

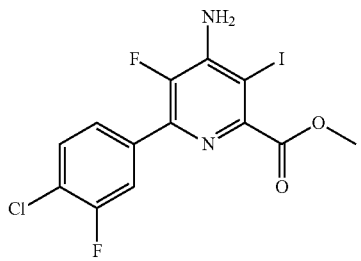 [SMILES: COC(=O)c1nc(-c2ccc(Cl)c(F)c2)c(F)c(N)c1I]

Methyl 4-amino-6-(4-chloro-3-fluorophenyl)-5-fluoropicolinate (3.1 g, 10.38 mmol) was dissolved in methanol (40 mL). Periodic acid (0.946 g, 4.15 mmol) and iodine (2.371 g, 9.34 mmol) were added. The reaction mixture was heated at reflux overnight. The cooled reaction mixture was diluted with dichloromethane and washed with 1N sodium sulfite. The organic phase was washed with 1N sodium sulfite, washed with saturated sodium chloride, dried over magnesium sulfate, fitered, and concentrated onto celite. The product was purified by flash chromatography (SiO₂, 100% dichloromethane) to provide the title compound 4.17 g, 9.82 mmol, 95% yield) as a pink solid: ¹H NMR (400 MHz, DMSO-d₆) d 3.88 (s, 3H), 6.80 (s, 2H), 7.65-7.77 (m, 2H), 7.77-7.84 (m, 1H); ¹⁹F NMR (376 MHz, DMSO-d₆) d −140.15 , −115.85. ESIMS m/z 426 ([M+H]⁺).

Other compounds prepared by the method of Example 22 include:

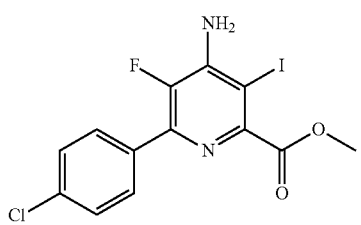 [SMILES: COC(=O)c1nc(-c2ccc(Cl)cc2)c(F)c(N)c1I]

Methyl 4-amino-6-(4-chlorophenyl)-5-fluoro-3-iodopicolinate: mp 110-111° C.; ¹H NMR (400 MHz, CDCl₃) δ 7.93-7.84 (m, 2H), 7.48-7.39 (m, 2H), 5.05 (s, 2H), 3.99 (s, 3H); ¹⁹F NMR (376 MHz, CDCl₃) δ −140.58 (s); ESIMS m/z 407 ([M+H]⁺).

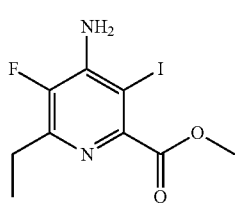

Methyl 4-amino-6-ethyl-5-fluoro-3-iodopicolinate: ¹H NMR (400 MHz, DMSO-d6) δ 1.14 (t, J=7.6 Hz, 2H), 2.63 (qd, J=7.6, 2.7 Hz, 1H), 3.34-3.42 (m, 7H), 3.83 (s, 2H), 6.46 (s, 1H); ¹⁹F NMR (376 MHz, DMSO-d6) δ −143.22; ESIMS m/z 323 ([M−H]⁻).

Example 23

Preparation of (E)-methyl 4-amino-6-(4-chloro-3-fluorophenyl)-5-fluoro-3-(2-(trimethylsilyl)vinyl) picolinate (Compound 11)

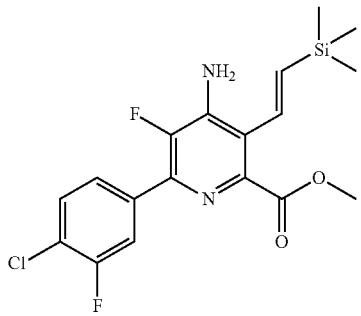 [SMILES: COC(=O)c1nc(-c2ccc(Cl)c(F)c2)c(F)c(N)c1/C=C/[Si](C)(C)C]

Methyl 4-amino-6-(4-chloro-3-fluorophenyl)-5-fluoro-3-iodopicolinate (350 mg, 0.824 mmol), and tetrakis triphenylphosphine palladium(0) (95 mg, 0.082 mmol) were combined in a Biotage microwave reaction vessel that was then sealed and purged with nitrogen. (E)-trimethyl(2-(tributylstannyl)vinyl)silane (417 mg, 1.072 mmol) in dioxane (4122 µl) was added and the reaction mixture was heated in a microwave reactor at 120° C. for 30 min The cooled reaction mixture was diluted with ethyl acetate and washed with saturated sodium chloride. The organic phase was dried over magnesium sulfate, filtered and concentrated on to silica. The product was purified by flash chromatography. (SiO₂, 0-20% EtOAc:Hex gradient) to provide the title compound as a tan solid (260 mg, 0.655 mmol, 79% yield); 1H NMR (400 MHz, DMSO-d6) d 0.17 (s, 9H), 3.76 (s, 3H), 6.09 (d, J=19.2 Hz, 1H), 6.60 (s, 2H), 6.91 (d, J=19.2 Hz, 1H), 7.75 (dd, J=3.8, 1.9 Hz, 2H), 7.83 (dd, J=10.8, 1.3 Hz, 1H); 19F NMR (376 MHz, DMSO-d6) d −145.16 , −115.98; ESIMS m/z 398 ([M+H]⁺).

Another compound prepared by the method of Example 23 is:

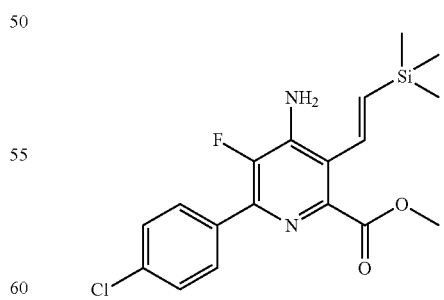

(E)-Methyl 4-amino-6-(4-chlorophenyl)-5-fluoro-3-(2-(trimethylsilyl)vinyl)picolinate (Compound 12): mp 113-115° C.;

¹H NMR (400 MHz, CDCl₃) δ 7.94-7.86 (m, 2H), 7.49-7.38 (m, 2H), 7.01 (d, J=19.8 Hz, 1H), 6.27 (d, J=19.8 Hz,

1H), 4.64 (s, 2H), 3.90 (s, 3H), 0.20 (s, 9H); $^{19}$F NMR (376 MHz, CDCl$_3$) δ −144.45; ESIMS m/z 379 ([M+H]$^+$).

Example 24

Preparation of (E)-methyl 4-amino-6-ethyl-5-fluoro-3-(2-(trimethylsilyl)vinyl)picolinate (Compound 13)

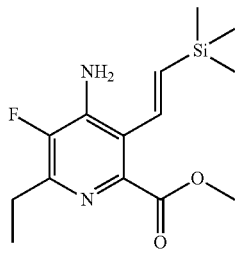 [SMILES: CCc1nc(C(=O)OC)c(/C=C/[Si](C)(C)C)c(N)c1F]

Methyl 4-amino-6-ethyl-5-fluoro-3-iodopicolinate (270 mg, 0.833 mmol) and bis(triphenylphosphine)palladium(II) dichloride (58.5 mg, 0.083 mmol) were combined in a microwave reactor vessel. (E)-trimethyl(2-(tributylstannyl)vinyl) silane (649 mg, 1.666 mmol) dissolved in dichloroethane (0.8 mL) was added and the reaction mixture was heated at 120° C. for 30 min a microwave reactor. The cooled reaction mixture was diluted with ethyl acetate and water. The aqueous phase was extracted three more times with ethyl acetate. The combined organic phases were dried over magnesium sulfate, filtered, and concentrated on to silica. The product was purifed by flash chromatography (SiO$_2$, 0-30% EtOAc:Hex gradient) to provide the title compound as an off-white solid (143 mg, 0.482 mmol, 57.9% yield): $^1$H NMR (400 MHz, DMSO-d6) δ 0.14 (s, 9H), 1.16 (t, J=7.6 Hz, 3H), 2.65 (qd, J=7.6, 2.6 Hz, 2H), 3.71 (s, 3H), 5.99 (d, J=19.3 Hz, 1H), 6.25 (s, 2H), 6.84 (d, J=19.2 Hz, 1H); $^{19}$F NMR (376 MHz, DMSO-d6) δ −148.85; ESIMS m/z 297 ([M+H]$^+$), 295 ([M−H]$^-$).

Example 25

Preparation of (E)-4-amino-6-(4-chloro-3-fluorophenyl)-5-fluoro-3-(2-(trimethylsilyl)vinyl)picolinic acid (Compound 14)

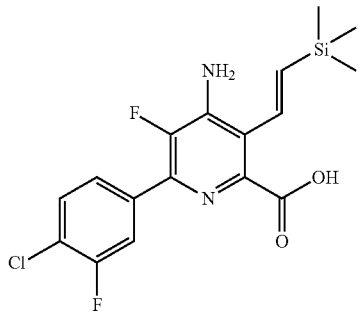 [SMILES: C[Si](C)(C)/C=C/c1c(C(=O)O)nc(-c2ccc(Cl)c(F)c2)c(F)c1N]

(E)-methyl 4-amino-6-(4-chloro-3-fluorophenyl)-5-fluoro-3-(2-(trimethylsilyl)vinyl)picolinate (169 mg, 0.426 mmol) was dissolved in methanol (2 mL), THF (2 mL) and Water (1 mL). Lithium hydroxide hydrate (93 mg, 2.216 mmol) was added. The reaction mixture was stirred at room temperature overnight. The reaction mixture was concentrated to dryness under vaccum. The resulting residue was partitioned between 1 N HCl and ethyl acetate. The aqueous phase was extracted three more times with ethyl acetate. The organic phases were combined, dried over magnesium sulfate, filtered, and concentrated under vacuum to provide the title compound as an off-white solid (146 mg, 0.381 mmol, 90% yield): $^1$H NMR (400 MHz, DMSO-d6) δ 0.17 (s, 9H), 6.26 (d, J=19.4 Hz, 1H), 6.49 (s, 2H), 6.93 (d, J=19.5 Hz, 1H), 7.68-7.83 (m, 2H), 7.88 (dd, J=10.9, 1.8 Hz, 1H); $^{19}$F NMR (376 MHz, DMSO-d6) δ −145.32, −116.04. ESIMS m/z 384 ([M+H]$^+$).

Other compounds prepared by the method of Example 25 include:

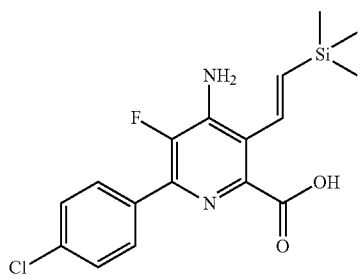 [SMILES: C[Si](C)(C)/C=C/c1c(C(=O)O)nc(-c2ccc(Cl)cc2)c(F)c1N]

(E)-4-amino-6-(4-chlorophenyl)-5-fluoro-3-(2-(trimethylsilyl)vinyl)picolinic acid (Compound 15): $^1$H NMR (400 MHz, CDCl$_3$) δ 7.86-7.83 (m, 2H), 7.50-7.46 (m, 2H), 7.42 (d, J=20.1 Hz, 1H), 6.29 (d, J=20.2 Hz, 1H), 4.93 (s, 2H), 0.24 (s, 9H); $^{19}$F NMR (376 MHz, CDCl$_3$) δ −141.35; ESIMS m/z 366 ([M+H]$^+$), 364 ([M−H]$^-$).

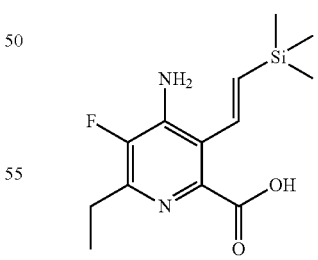

(E)-4-amino-6-ethyl-5-fluoro-3-(2-(trimethylsilyl)vinyl) picolinic acid (Compound 16): $^1$H NMR (400 MHz, DMSO-d6) δ 0.14 (s, 9H), 1.18 (t, J=7.6 Hz, 3H), 2.61-2.72 (m, 2H), 6.12-6.23 (m, 3H), 6.88 (d, J=19.4 Hz, 1H), 12.91 (s, 1H); $^{19}$F NMR (376 MHz, DMSO-d6) δ −149.02; ESIMS m/z 283 ([M+H]$^+$), 281 ([M−H]$^-$).

TABLE 1

| Compound No. | Name | Structure |
|---|---|---|
| 1 | (E)-methyl 6-amino-2-(4-chloro-2,3-difluorophenyl)-5-(2-(trimethylsilyl)vinyl)-pyrimidine-4-carboxylate | 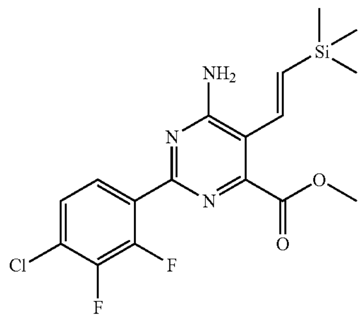 [SMILES: COC(=O)c1nc(-c2ccc(Cl)c(F)c2F)nc(N)c1/C=C/[Si](C)(C)C] |
| 2 | (E)-methyl 6-amino-2-(4-chloro-2-fluoro-3-methoxyphenyl)-5-(2-(trimethylsilyl)vinyl)-pyrimidine-4-carboxylate | 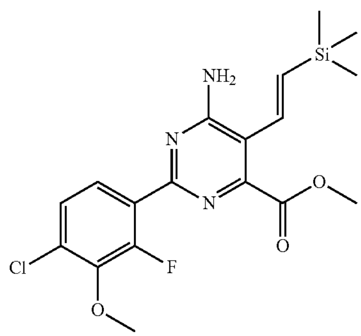 [SMILES: COC(=O)c1nc(-c2ccc(Cl)c(OC)c2F)nc(N)c1/C=C/[Si](C)(C)C] |
| 3 | (E)-methyl 6-amino-2-(4-chloro-2-fluorophenyl)-5-(2-(trimethylsilyl)vinyl)-pyrimidine-4-carboxylate | 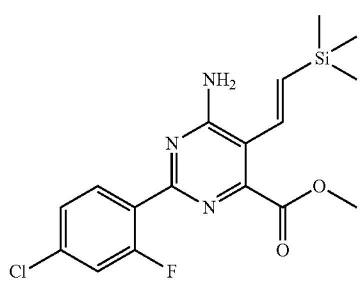 [SMILES: COC(=O)c1nc(-c2ccc(Cl)cc2F)nc(N)c1/C=C/[Si](C)(C)C] |
| 4 | (E)-ethyl 6-amino-2-cyclopropyl-5-(2-(trimethylsilyl)vinyl)-pyrimidine-4-carboxylate | 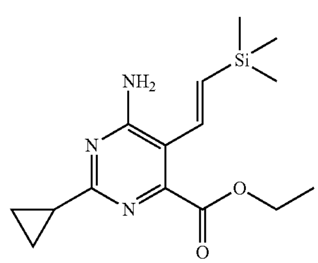 [SMILES: CCOC(=O)c1nc(C2CC2)nc(N)c1/C=C/[Si](C)(C)C] |
| 5 | (E)-6-amino-2-(4-chloro-2,3-difluorophenyl)-5-(2-(trimethylsilyl)vinyl)-pyrimidine-4-carboxylic acid | 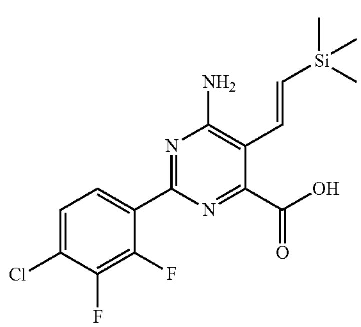 [SMILES: C[Si](C)(C)/C=C/c1c(N)nc(-c2ccc(Cl)c(F)c2F)nc1C(=O)O] |

TABLE 1-continued

| Compound No. | Name | Structure |
|---|---|---|
| 6 | (E)-6-amino-2-(4-chloro-2-fluoro-3-methoxyphenyl)-5-(2-(trimethylsilyl)vinyl)-pyrimidine-4-carboxylic acid | 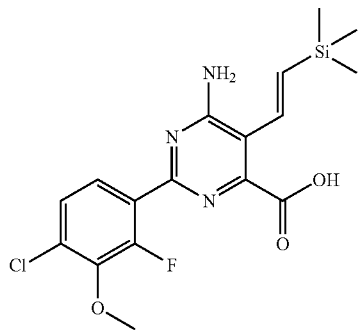 [SMILES: COc1c(Cl)ccc(-c2nc(N)c(/C=C/[Si](C)(C)C)c(C(=O)O)n2)c1F] |
| 7 | (E)-6-amino-2-(4-chloro-2-fluorophenyl)-5-(2-(trimethylsilyl)vinyl)-pyrimidine-4-carboxylic acid | 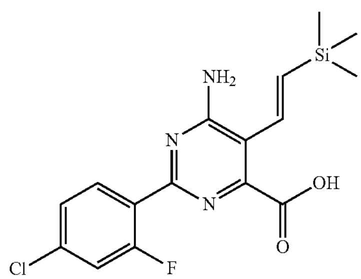 [SMILES: C[Si](C)(C)/C=C/c1c(N)nc(-c2ccc(Cl)cc2F)nc1C(=O)O] |
| 8 | (E)-6-amino-2-cyclopropyl-5-(2-(trimethylsilyl)vinyl)pyrimidine-4-carboxylic acid | 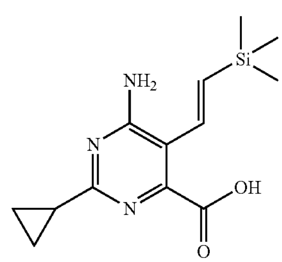 [SMILES: C[Si](C)(C)/C=C/c1c(N)nc(C2CC2)nc1C(=O)O] |
| 9 | (E)-methyl 6-amino-2-(4-chloro-2-fluoro-3-methoxyphenyl)-5-(2-(triethoxysilyl)vinyl)-pyrimidine-4-carboxylate | 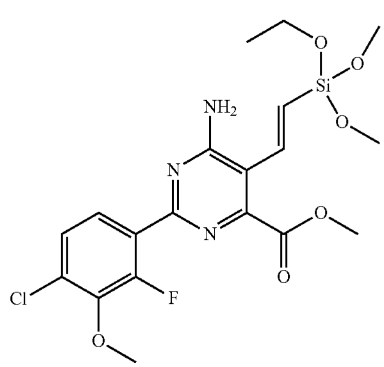 [SMILES: CCO[Si](/C=C/c1c(N)nc(-c2ccc(Cl)c(OC)c2F)nc1C(=O)OC)(OC)OC] |

TABLE 1-continued

| Compound No. | Name | Structure |
|---|---|---|
| 10 | (E)-6-amino-2-(4-chloro-2-fluoro-3-methoxyphenyl)-5-(2-(trihydroxysilyl)vinyl)pyrimidine-4-carboxylic acid | 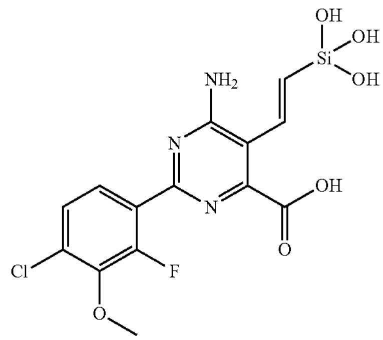 [SMILES: COc1c(Cl)ccc(-c2nc(N)c(/C=C/[Si](O)(O)O)c(C(=O)O)n2)c1F] |
| 11 | (E)-methyl 4-amino-6-(4-chloro-3-fluorophenyl)-5-fluoro-3-(2-(trimethylsilyl)vinyl)picolinate | 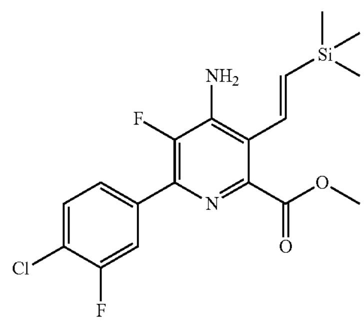 [SMILES: COC(=O)c1nc(-c2ccc(Cl)c(F)c2)c(F)c(N)c1/C=C/[Si](C)(C)C] |
| 12 | (E)-methyl 4-amino-6-(4-chlorophenyl)-5-fluoro-3-(2-(trimethylsilyl)vinyl)picolinate | 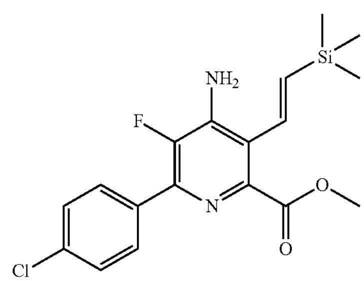 |
| 13 | (E)-methyl 4-amino-6-ethyl-5-fluoro-3-(2-(trimethylsilyl)vinyl)picolinate | 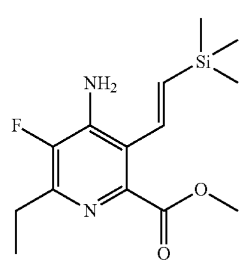 [SMILES: CCc1nc(C(=O)OC)c(/C=C/[Si](C)(C)C)c(N)c1F] |
| 14 | (E)-4-amino-6-(4-chloro-3-fluorophenyl)-5-fluoro-3-(2-(trimethylsilyl)vinyl)-picolinic acid | 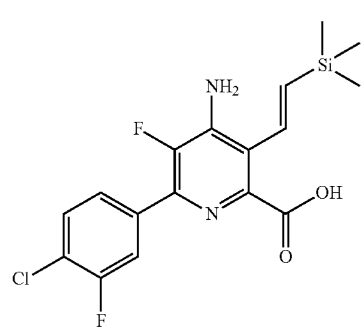 [SMILES: C[Si](C)(C)/C=C/c1c(C(=O)O)nc(-c2ccc(Cl)c(F)c2)c(F)c1N] |

TABLE 1-continued

Compound number and structure

| Compound No. | Name | Structure |
|---|---|---|
| 15 | (E)-4-amino-6-(4-chlorophenyl)-5-fluoro-3-(2-(trimethylsilyl)vinyl)-picolinic acid | 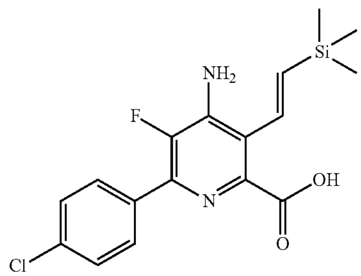 [SMILES: C[Si](C)(C)/C=C/c1c(C(=O)O)nc(-c2ccc(Cl)cc2)c(F)c1N] |
| 16 | (E)-4-amino-6-ethyl-5-fluoro-3-(2-(trimethylsilyl)-vinyl)picolinic acid | 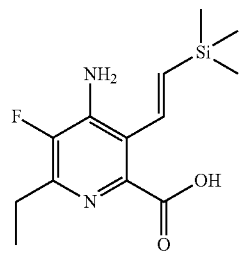 [SMILES: CCc1nc(C(=O)O)c(/C=C/[Si](C)(C)C)c(N)c1F] |

Preparation of Herbicidal Compositions

In the following illustrative compositions, parts and percentages are by weight.

Emulsifiable Concentrates

Formulation A

| | T % |
|---|---|
| Compound 1 | 6.2 |
| Polyglycol 26-3 Nonionic emulsifier-(di-sec-butyl)-phenyl-poly(oxypropylene)block polymer with (oxyethylene). The polyoxyethelene content is about 12 moles. | 5.2 |
| Witconate P12-20 (Anionic emulsifier-calcium dodecylbenzene sulfonate-60 wt. % active) | 5.2 |
| Aromatic 100 (Xylene range aromatic solvent) | 3.4 |

Formulation B

| | WT % |
|---|---|
| Compound 2 | 3.5 |
| Sunspray 11N (paraffin oil) | 40.0 |
| Polyglycol 26-3 | 19.0 |
| Oleic acid | 1.0 |
| Xylene range aromatic solvent | 36.5 |

Formulation C

| | T % |
|---|---|
| Compound 2 | 3.2 |
| Stepon C-65 | 5.7 |
| Ethomeen T/25 | 7.7 |
| Ethomeen T/15 | 8.0 |
| Xylene range aromatic solvent | 5.4 |

Formulation D

| | T % |
|---|---|
| Compound 1 | 0.0 |
| Agrimer Al-10LC (emulsifier) | .0 |
| N-methyl-2-pyrrolidone | 7.0 |

Formulation E

| | WT % |
|---|---|
| Compound 2 | 10.0 |
| Agrimul 70-A (dispersant) | 2.0 |
| Amsul DMAP 60 (thickener) | 2.0 |
| Emulsogen M (emulsifier) | 8.0 |
| Attagel 50 (suspension aid) | 2.0 |
| Crop oil | 76.0 |

These concentrates can be diluted with water to give emulsions of suitable concentrations for controlling weeds.

Wettable Powders
Formulation F

|  | T % |
| --- | --- |
| Compound 3 | 6.0 |
| Polyglycol 26-3 | 2.0 |
| Polyfon H | 4.0 |
| Zeosyl 100 (Precipitated hydrated SiO$_2$) | 17.0 |
| Barden clay + inerts | 51.0 |

Formulation G

|  | WT % |
| --- | --- |
| Compound 4 | 62.4 |
| Polyfon H (sodium salt of lignin sulfonate) | 6.0 |
| Sellogen HR (sodium naphthalene sulfonate) | 4.0 |
| Zeosyl 100 | 27.6 |

Formulation H

|  | WT % |
| --- | --- |
| Compound 3 | 1.4 |
| Kunigel V1 (carrier) | 30.0 |
| Stepanol ME Dry (wetter) | 2.0 |
| Tosnanon GR 31A (binder) | 2.0 |
| Kaolin NK-300 Clay (filler) | 64.6 |

The active ingredient is applied to the corresponding carriers and then these are mixed and ground to yield wettable powders of excellent wettability and suspension power. By diluting these wettable powders with water it is possible to obtain suspensions of suitable concentrations for controlling weeds.

Water Dispersible Granules
Formulation I

|  | T % |
| --- | --- |
| Compound 3 | 6.0 |
| Sellogen HR | 4.0 |
| Polyfon H | 5.0 |
| Zeosyl 100 | 7.0 |
| Kaolinite clay | 8.0 |

The active ingredient is added to the hydrated silica, which is then mixed with the other ingredients and ground to a powder. The powder is agglomerated with water and sieved to provide granules in the range of −10 to +60 mesh. By dispersing these granules in water it is possible to obtain suspensions of suitable concentrations for controlling weeds.

Granules
Formulation J

|  | T % |
| --- | --- |
| Compound 4 | 5.0 |
| Celetom MP-88 | 5.0 |

The active ingredient is applied in a polar solvent such as N-methylpyrollidinone, cyclohexanone, gamma-butyrolactone, etc. to the Celetom MP 88 carrier or to other suitable carriers. The resulting granules can be applied by hand, granule applicator, airplane, etc. in order to control weeds.

Formulation K

|  | T % |
| --- | --- |
| Compound 3 | 1.0 |
| Polyfon H | 8.0 |
| Nekal BA 77 | 2.0 |
| Zinc Stearate | 2.0 |
| Barden Clay | 7.0 |

All materials are blended and ground to a powder then water is added and the clay mixture is stirred until a paste is formed. The mixture is extruded through a die to provide granules of proper size.

Water Soluble Liquids
Formulation L

|  | T % |
| --- | --- |
| Compound 3 | .67 |
| Monoethanolamine pH buffer | 0.5 |
| Water | 5.83 |

The active ingredient is dissolved in an appropriate amount of water and the additional monoethanolamine is added as a buffer. A water-soluble surfactant may be added. Other aids may be incorporated to improve physical, chemical and/or formulation properties.

Evaluation of Postemergence Herbicidal Activity

Seeds or nutlets of the desired test plant species were planted in Sun Gro MetroMix® 306 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7-21 days in a greenhouse with an approximate 15 hour photoperiod which was maintained at about 23-29° C. during the day and 22-28° C. during the night. Nutrients and water were added on a regular basis and supplemental lighting was provided with overhead metal halide 1000-Watt lamps as necessary. The plants were employed for testing when they reached the first or second true leaf stage.

A weighed amount, determined by the highest rate to be tested, of each test compound was placed in a 25 mL glass vial and was dissolved in 4 mL of a 97:3 v/v (volume/volume) mixture of acetone and dimethyl sulfoxide (DMSO) to obtain concentrated stock solutions. If the test compound did not dissolve readily, the mixture was warmed and/or sonicated. The concentrated stock solutions obtained were diluted with 20 mL of an aqueous mixture containing acetone, water, isopropyl alcohol, DMSO, Atplus 411F crop oil concentrate, and Triton® X-155 surfactant in a 48.5:39:10:1.5:1.0:0.02 v/v ratio to obtain spray solutions containing the highest application rates. Additional application rates were obtained by serial dilution of 12 mL of the high rate solution into a solution containing 2 mL of 97:3 (v/v) mixture of acetone and dimethyl sulfoxide (DMSO) and 10 mL of an aqueous mixture containing acetone, water, isopropyl alcohol, DMSO, Atplus 411F crop oil concentrate, and Triton X-155 surfactant in a 48.5:39:10:1.5:1.0:0.02 (v/v) ratio to obtain 1/2 ×, 1/4 ×, 1/8× and 1/16× rates of the high rate. Compound requirements are based upon a 12 mL application volume at a rate of 187 L/ha. Formulated compounds were applied to the plant material with an overhead Mandel track sprayer equipped with a 8002E nozzles calibrated to deliver 187 L/ha over an application area of 0.503 square meters at a spray height of 18 inches (43 cm) above the average plant canopy height. Control plants were sprayed in the same manner with the solvent blank.

The treated plants and control plants were placed in a greenhouse as described above and watered by sub-irrigation to prevent wash-off of the test compounds. After 14 days, the condition of the test plants as compared with that of the untreated plants was determined visually and scored on a scale of 0 to 100 percent where 0 corresponds to no injury and 100 corresponds to complete kill By applying the well-accepted probit analysis as described by J. Berkson in *Journal of the American Statistical Society*, 48, 565 (1953) and by D. Finney in *"Probit Analysis"* Cambridge University Press (1952), the above data can be used to calculate $GR_{50}$ and $GR_{80}$ values, which are defined as growth reduction factors that correspond to the effective dose of herbicide required to kill or control 50 percent or 80 percent, respectively, of a target plant. Some of the compounds tested, application rates employed, plant species tested, and results are given in Table 3 and Table 4.

TABLE 3

Post-emergent control of weeds.

| Compound # | Rate (g ai/ha) | % Growth Reduction | | | |
|---|---|---|---|---|---|
| | | ABUTH | AMARE | ECHCG | HELAN |
| 1 | 140 | 100 | 100 | 85 | 90 |
| 2 | 140 | 98 | 100 | 98 | 100 |
| 3 | 140 | 100 | 100 | 0 | 90 |
| 4 | 140 | 0 | NT[1] | 0 | 0 |
| 5 | 140 | 100 | 90 | 50 | 90 |
| 6 | 140 | 100 | 100 | 100 | 100 |
| 7 | 140 | 100 | 100 | 80 | 90 |
| 8 | 280 | 0 | NT | 0 | 65 |
| 9 | 140 | 100 | NT | 80 | 90 |
| 10 | 140 | 100 | NT | 80 | 100 |
| 11 | 140 | 80 | 100 | 0 | 90 |
| 12 | 140 | 90 | 75 | 0 | 90 |
| 14 | 140 | 65 | NT | 70 | 80 |
| 15 | 140 | 80 | 100 | 80 | 90 |
| 16 | 280 | 5 | NT | 0 | 20 |

[1]Not Tested
ABUTH = velvetleaf (*Abutilon theophrasti*)
AMARE = redroot pigweed (*Amaranthus retroflexus*)
ECHCG = barnyardgrass (*Echinochloa crus-galli*)
HELAN = sunflower (*Helianthus annuus*)

TABLE 4

Post-emergent control of weeds.

| Compound # | Rate (g ai/ha) | % Growth Reduction | | |
|---|---|---|---|---|
| | | CHEAL | IPOHE | EPHHL |
| 1 | 140 | 100 | 80 | 50 |
| 2 | 140 | NT[1] | 90 | 100 |
| 3 | 140 | 100 | 70 | 100 |
| 4 | 140 | 100 | 100 | 100 |
| 5 | 140 | 100 | 60 | 100 |
| 6 | 140 | 100 | 95 | 100 |
| 7 | 140 | 100 | 70 | 100 |
| 8 | 280 | 65 | 78 | 100 |
| 9 | 140 | 100 | 80 | 100 |
| 10 | 140 | 100 | 80 | 100 |
| 11 | 140 | 100 | 70 | 80 |
| 12 | 140 | 100 | 0 | 80 |
| 14 | 140 | 100 | 80 | 100 |
| 15 | 140 | 90 | 70 | 90 |
| 16 | 280 | 10 | 60 | 0 |

[1]Not Tested
CHEAL = lambsquarters (*Chenopodium album*)
IPOHE = ivyleaf morningglory (*Ipomoea hederacea*)
EPHHL = wild poinsettia (*Euphorbia heterophylla*)

The foregoing is illustrative of the present invention, and is not to be construed as limiting thereof. The invention is defined by the following claims, with equivalents of the claims to be included therein.

What is claimed is:

1. A compound of the Formula I

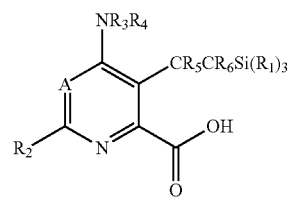

wherein
A is selected from the group consisting of nitrogen and $CR_5$;
Each $R_1$ is independently selected from the group consisting of $C_1$-$C_{10}$ alkyl, $C_3$-$C_6$ cycloalkyl, $C_1$-$C_{10}$ haloalkyl, $C_3$-$C_6$ halocycloalkyl, substituted or unsubstituted phenyl, $C_1$-$C_{10}$ alkoxy, and hydroxy ($R_1$ groups can but need not be equivalent);
$R_2$ is selected from the group consisting of $C_1$-$C_6$ alkyl, $C_3$-$C_6$ cycloalkyl, $C_1$-$C_6$ haloalkyl, $C_3$-$C_6$ halocycloalkyl, and

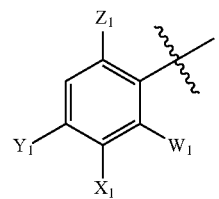

wherein
$W_1$ is selected from the group consisting of hydrogen and fluorine; $X_1$ is selected from the group consisting of hydrogen, halogen, $C_1$-$C_6$ alkyl, $C_2$-$C_6$ alkenyl, $C_2$-$C_6$ alkynyl, $C_1$-$C_6$ alkoxy, $C_2$-$C_4$ alkoxyalkyl, $C_2$-$C_6$ alkylcarbonyl, $C_1$-$C_6$ alkylthio, $C_1$-$C_6$ alkylsulfinyl, $C_1$-$C_6$ alkylsulfonyl, $C_2$-$C_4$ alkenyloxy, $C_2$-$C_4$ alkynloxy, $C_2$-$C_4$ alkenylthio, $C_2$-$C_4$ alkynylthio, $C_1$-$C_6$ haloalkyl, $C_2$-$C_6$ haloalkenyl, $C_2$-$C_6$ haloalkynyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_4$ haloalkenyloxy, $C_2$-$C_4$ haloalkynyloxy, $C_2$-$C_4$ haloalkenylthio, $C_2$-$C_4$ haloalkynylthio, and —$N(R_7)_2$; $Y_1$ is selected from the group consiting of hydrogen, halogen, $C_1$-$C_6$ alkyl, $C_1$-$C_6$ haloalkyl, $C_1$-$C_6$ alkoxy, $C_1$-$C_6$ haloalkoxy; $Z_1$ is selected from the group consisting of hydrogen and fluorine; and wherein when $X_1$ and $Y_1$ are selected from the group consisting of —$O(CH_2)_nCH_2$— or —$O(CH_2)_nO$— wherein n=1 or 2;

$R_3$ and $R_4$ are selected independently from the group consisting of hydrogen, $C_1$-$C_6$ alkyl, $C_3$-$C_6$ alkenyl, $C_3$-$C_6$ alkynyl, hydroxy, $C_1$-$C_6$ alkoxy, amino, $C_1$-$C_6$ acyl, $C_1$-$C_6$ carboalkoxy, $C_1$-$C_6$ alkylcarbamyl, $C_1$-$C_6$ alkylsulfonyl, $C_1$-$C_6$ trialkylsilyl, and $C_1$-$C_6$ dialkyl phosphonyl;

$R_5$ is selected from the group consisting of hydrogen, fluorine, and chlorine;

$R_6$ is selected from the group consisting of hydrogen, fluorine, chlorine, $C_1$-$C_4$ alkyl, and $C_1$-$C_4$ haloalkyl; and $R_7$ is selected from the group consisting of hydrogen, $C_1$-$C_4$ alkyl and $C_1$-$C_4$ haloalkyl.

2. The compound of claim 1 further comprising an agriculturally acceptable derivative of the carboxylic acid group.

3. An agricultural composition comprising a compound of Formula I

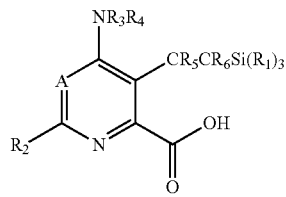

I wherein

A is selected from the group consisting of nitrogen and $CR_5$;

Each $R_1$ is independently selected from the group consisting of $C_1$-$C_{10}$ alkyl, $C_3$-$C_6$ cycloalkyl, $C_1$-$C_{10}$ haloalkyl, $C_3$-$C_6$ halocycloalkyl, substituted or unsubstituted phenyl, $C_1$-$C_{10}$ alkoxy, and hydroxy ($R_1$ groups can but need not be equivalent);

$R_2$ is selected from the group consisting of $C_1$-$C_6$ alkyl, $C_3$-$C_6$ cycloalkyl, $C_1$-$C_6$ haloalkyl, $C_3$-$C_6$ halocycloalkyl, and

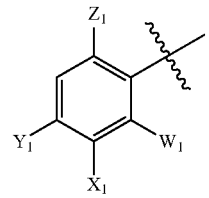

wherein $W_1$ is selected from the group consisting of hydrogen and fluorine; $X_1$ is selected from the group consisting of hydrogen, halogen, $C_1$-$C_6$ alkyl, $C_2$-$C_6$ alkenyl, $C_2$-$C_6$ alkynyl, $C_1$-$C_6$ alkoxy, $C_2$-$C_4$ alkoxyalkyl, $C_2$-$C_6$ alkylcarbonyl, $C_1$-$C_6$ alkylthio, $C_1$-$C_6$ alkylsulfinyl, $C_1$-$C_6$ alkylsulfonyl, $C_2$-$C_4$ alkenyloxy, $C_2$-$C_4$ alkynloxy, $C_2$-$C_4$ alkenylthio, $C_2$-$C_4$ alkynylthio, $C_1$-$C_6$ haloalkyl, $C_2$-$C_6$ haloalkenyl, $C_2$-$C_6$ haloalkynyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_4$ haloalkenyloxy, $C_2$-$C_4$ haloalkynyloxy, $C_2$-$C_4$ haloalkenylthio, $C_2$-$C_4$ haloalkynylthio, and —$N(R_7)_2$; $Y_1$ is selected from the group consiting of hydrogen, halogen, $C_1$-$C_6$ alkyl, $C_1$-$C_6$ haloalkyl, $C_1$-$C_6$ alkoxy, $C_1$-$C_6$ haloalkoxy; $Z_1$ is selected from the group consisting of hydrogen and fluorine; and wherein when $X_1$ and $Y_1$ are selected from the group consisting of —$O(CH_2)_nCH_2$— or —$O(CH_2)_nO$— wherein n=1 or 2;

$R_3$ and $R_4$ are selected independently from the group consisting of hydrogen, $C_1$-$C_6$ alkyl, $C_3$-$C_6$ alkenyl, $C_3$-$C_6$ alkynyl, hydroxy, $C_1$-$C_6$ alkoxy, amino, $C_1$-$C_6$ acyl, $C_1$-$C_6$ carboalkoxy, $C_1$-$C_6$ alkylcarbamyl, $C_1$-$C_6$ alkylsulfonyl, $C_1$-$C_6$ trialkylsilyl, and $C_1$-$C_6$ dialkyl phosphonyl;

$R_5$ is selected from the group consisting of hydrogen, fluorine, and chlorine;

$R_6$ is selected from the group consisting of hydrogen, fluorine, chlorine, $C_1$-$C_4$ alkyl, and $C_1$-$C_4$ haloalkyl; and $R_7$ is selected from the group consisting of hydrogen, $C_1$-$C_4$ alkyl and $C_1$-$C_4$ haloalkyl.

4. The composition of claim 3, wherein said composition is administered in an amount sufficient to control the growth of a weed.

5. The composition of claim 3 further comprising an agriculturally acceptable derivative of the carboxylic acid group.

6. A method of controlling a weed comprising administering to a field an effective amount of a compound of Formula I

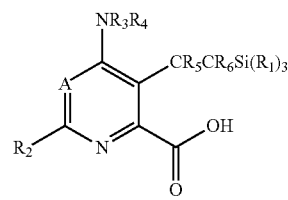

I wherein
- A is selected from the group consisting of nitrogen and $CR_5$;
- Each $R_1$ is independently selected from the group consisting of $C_1$-$C_{10}$alkyl, $C_3$-$C_6$ cycloalkyl, $C_1$-$C_{10}$ haloalkyl, $C_3$-$C_6$ halocycloalkyl, substituted or unsubstituted phenyl, $C_1$-$C_{10}$ alkoxy, and hydroxy ($R_1$ groups can but need not be equivalent);
- $R_2$ is selected from the group consisting of $C_1$-$C_6$ alkyl, $C_3$-$C_6$ cycloalkyl, $C_1$-$C_6$ haloalkyl, $C_3$-$C_6$ halocycloalkyl, and

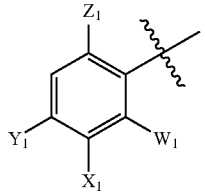

wherein
- $W_1$ is selected from the group consisting of hydrogen and fluorine; $X_1$ is selected from the group consisting of hydrogen, halogen, $C_1$-$C_6$ alkyl, $C_2$-$C_6$ alkenyl, $C_2$-$C_6$ alkynyl, $C_1$-$C_6$ alkoxy, $C_2$-$C_4$ alkoxyalkyl, $C_2$-$C_6$ alkylcarbonyl, $C_1$-$C_6$ alkylthio, $C_1$-$C_6$ alkylsulfinyl, $C_1$-$C_6$ alkylsulfonyl, $C_2$-$C_4$ alkenyloxy, $C_2$-$C_4$ alkynloxy, $C_2$-$C_4$ alkenylthio, $C_2$-$C_4$ alkynylthio, $C_1$-$C_6$ haloalkyl, $C_2$-$C_6$ haloalkenyl, $C_2$-$C_6$ haloalkynyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_4$ haloalkenyloxy, $C_2$-$C_4$ haloalkynyloxy, $C_2$-$C_4$ haloalkenylthio, $C_2$-$C_4$ haloalkynylthio, and $-N(R_7)_2$; $Y_1$ is selected from the group consiting of hydrogen, halogen, $C_1$-$C_6$ alkyl, $C_1$-$C_6$ haloalkyl, $C_1$-$C_6$ alkoxy, $C_1$-$C_6$ haloalkoxy; $Z_1$ is selected from the group consisting of hydrogen and fluorine; and wherein when $X_1$ and $Y_1$ are selected from the group consisting of $-O(CH_2)_nCH_2-$ or $-O(CH_2)_nO-$ wherein n=1 or 2;
- $R_3$ and $R_4$ are selected independently from the group consisting of hydrogen, $C_1$-$C_6$ alkyl, $C_3$-$C_6$ alkenyl, $C_3$-$C_6$ alkynyl, hydroxy, $C_1$-$C_6$ alkoxy, amino, $C_1$-$C_6$ acyl, $C_1$-$C_6$ carboalkoxy, $C_1$-$C_6$ alkylcarbamyl, $C_1$-$C_6$ alkylsulfonyl, $C_1$-$C_6$ trialkylsilyl, and $C_1$-$C_6$ dialkyl phosphonyl;
- $R_5$ is selected from the group consisting of hydrogen, fluorine, and chlorine;
- $R_6$ is selected from the group consisting of hydrogen, fluorine, chlorine, $C_1$-$C_4$ alkyl, and $C_1$-$C_4$ haloalkyl; and
- $R_7$ is selected from the group consisting of hydrogen, $C_1$-$C_4$ alkyl and $C_1$-$C_4$ haloalkyl.

7. The method according to claim 6, wherein the weed is selected from the group consisting of woody plants, grasses, sedges and broadleaf weeds.

8. The method according to claim 6, further comprising an agriculturally acceptable derivative of the carboxylic acid group.

9. The method according to claim 6, wherein Formula I is administered prior to emergence of the weed.

10. The method according to claim 6, wherein Formula I is administered post-emergence of the weed.

11. The method according to claim 6, wherein Formula I is administered directly to the weed.

12. A composition comprising the compound of Formula I of claim 3 further comprising at least one compound selected from the group consisting of fungicides, insecticides, nematocides, miticides, arthropodicides, and bactericides.

13. A method of controlling undesirable vegetation which comprises contacting the vegetation or the locus thereof with or applying to the soil to prevent the emergence of vegetation an herbicidally effective amount of a compound according to claim 1.

14. A mixture comprising the compound of claim 1 and an agriculturally acceptable adjuvant or carrier.

15. A mixture comprising the composition of claim 12 and an agriculturally acceptable adjuvant or carrier.

16. A The method according to claim 6 further comprising at least one compound selected from the group consisting of fungicides, insecticides, nematocides, miticides, arthropodicides, and bactericides.

* * * * *